(12) United States Patent
Lau et al.

(10) Patent No.: US 9,861,604 B2
(45) Date of Patent: Jan. 9, 2018

(54) CORIOLUS VERSICOLOR EXTRACTS, METHODS OF ISOLATING BIOLOGICALLY-ACTIVE COMPOUNDS, AND USES THEREOF

(71) Applicants: PURAPHARM COMPANY LIMITED, Hong Kong (CN); VERSITECH LIMITED, Hong Kong (CN); Maureen Lau, Hong Kong (CN)

(72) Inventors: Allan Sik Yin Lau, Hong Kong (CN); Lai Hung Cindy Yang, Hong Kong (CN); Stanley Chi Chung Chik, Hong Kong (CN)

(73) Assignees: BAGI RESEARCH LIMITED, Hong Kong (CN); VERSITECH LIMITED, Hong Kong (CN)

( * ) Notice: Subject to any disclaimer, the term of this patent is extended or adjusted under 35 U.S.C. 154(b) by 0 days.

(21) Appl. No.: 14/305,811

(22) Filed: Jun. 16, 2014

(65) Prior Publication Data

US 2014/0364499 A1 Dec. 11, 2014

Related U.S. Application Data

(62) Division of application No. 13/804,103, filed on Mar. 14, 2013, now abandoned.

(60) Provisional application No. 61/622,846, filed on Apr. 11, 2012.

(51) Int. Cl.
*A61K 31/231* (2006.01)
*C11B 1/10* (2006.01)
*C11C 1/00* (2006.01)

(52) U.S. Cl.
CPC .............. *A61K 31/231* (2013.01); *C11B 1/10* (2013.01); *C11C 1/002* (2013.01); *Y02P 20/582* (2015.11)

(58) Field of Classification Search
None
See application file for complete search history.

(56) References Cited

U.S. PATENT DOCUMENTS 6,348,609 B1 2/2002 Rombi

FOREIGN PATENT DOCUMENTS

| CN | 101613266 A | 12/2009 |
| CN | 101670116 A | 3/2010 |
| CN | 102204918 A | 10/2011 |

(Continued)

OTHER PUBLICATIONS

Sikorski, Conjugated Linoleic Acid (CLA) inhibits new vessel growth in the mammalian brain, Brain Research, 2008, 1213, pp. 35-40.*

(Continued)

*Primary Examiner* — Kathrien Cruz
*Assistant Examiner* — Andrew Lee
(74) *Attorney, Agent, or Firm* — Saliwanchik, Lloyd & Eisenschenk

(57) ABSTRACT

The subject invention provides efficient and convenient methods of isolating 9-oxo-10E, 12E-octadecadienoic acid methyl ester (9-KODE methyl ester) from *C. versicolor*. In addition, the subject invention provides therapeutic uses of *Coriolus versicolor* extracts, biologically-active chemical substituents isolated from *C. versicolor*, as well as 9-KODE methyl ester and related compounds. In a preferred embodiment, the subject invention can be used to inhibit the metastatic spread of cancer cells.

6 Claims, 20 Drawing Sheets

(56) References Cited

FOREIGN PATENT DOCUMENTS

| JP | 2005-162668 A | 6/2005 |
|---|---|---|
| WO | WO 2007/107856 A1 | 9/2007 |
| WO | WO 2008/078453 A1 | 7/2008 |

OTHER PUBLICATIONS

Simone, Oncology: Introduction, Cecil Textbook of Medicine, 20th Edition, 1996 vol. 1, pp. 1004-1010.*
Goncalves, Daniela C., et al., "Conjugated Linoleic Acid: good or bad nutrient." *Diabetology & Metabolic Syndrome*, 2010, 2(62):1-2.
Tokita, Masako et al. "New Geometric Isomers of Oxooctadecadienoate in Copper-Catalyzed Decomposition Products of Linoleate Hydroperoxide," *Bioscience, Biotechnology, and Biochemistry*, 1999, 63(6):993-997.
Doolittle, R.E. et al. "Determination of Double Bond Position in Conjugated Dienes by Chemical Ionization Mass Spectrometry with Isobutane," *Analytical Chemistry*, Jul. 1985, 57(8):1625-1630.
Harhaji, Lj et al., "Anti-tumor effect of *Coriolus versicolor* methanol extract against mouse B16 melanoma cells: in vitro and in vivo study," *Food and Chemical Toxicology*, 2008, 46:1825-1833.
Ho, Cheong-Yip et al., "*Coriolus versicolor* (Yunzhi) extract attenuates growth of human leukemia xenografts and induces apoptosis through the mitochondrial pathway," *Oncology Reports*, 2006, 16:609-616.
Schieberle, Peter et al. "Decomposition of Linoleic Acid Hydroperoxides by Radicals," *Z. Lebensm. Unters. Forsch.*, 1979, 168:448-456.
Supplementary Partial European Search Report for European Patent Application No. 13 77 5555, dated Oct. 9, 2015, in which references R1-R4 were cited by the European Examiner.
Böeseken, J. et al., "La réduction catalytique des acides α- et β-éléostéariques sous l'influence du nickel," *Recueil des Travaux Chimiques des Pays-Bas*, Sep. 1930, 49(3):247-256.
Ley, Steven V. et al., "Synthesis of β-dimorphecolic acid exploiting highly stereoselective reduction of a side-chain carbonyl group in a π-allyltricarbonyliron lactone complex," *J. Chem. Soc., Perkin Trans.* 1, Jan. 1997, 8(1):1125-1134.
Nakanishi, Naoaki et al., "Regioselective ϵ-Alkylation of 5-Acetoxy-1,3-alkadienes by Organocopper-Magnesium Reagents," *J. Org. Chem.*, May 1991, 56:3278-3283.
Smith, C.R. et al., "Dimorphecolic Acid—A Unique Hydroxydienoid Fatty Acid," *Journal of the American Chemical Society*, Mar. 1960, 82(6):1417-1421.
Watanebe, Jun et al., "9-Oxooctadeca-10,12-dienoic Acids as Acetyl-CoA Carboxylase Inhibitors from Red Pepper (*Capsicum annum* L.)," *Biosci. Biotechnol. Biochem.*, Jan. 1999, 63(3):489-493.
Extended European Search Report dated Feb. 23, 2016, for corresponding European Patent Application No. 13775555.9, in which references R1-R5 were cited by the Examiner in Europe.
Breton, Tony et al., "Allylic oxidation: easy synthesis of alkenones from activated alkenes with TEMPO," *Tetrahedron Letters*, 2005, 46:2487-2490.
Tassignon, P. et al., "Synthesis of the 9-oxo-diene derivative of methyl dimorphecolate by an efficient Oppenauer oxidation procedure," *Chemistry and Physics of Lipids*, 1994, 74:39-42.
De La Torre, A. et al. "Conjugated Linoleic Acid Isomers and their Conjugated Derivatives Inhibit Growth of Human Cancer Cell Lines." *Anticancer Research*, 2005, 25: 3943-3950.
Islam, M.A., et al. "Superior Anticarcinogenic Activity of trans, trans-Conjugated Linoleic Acid in N-Mthyl-N-nitrosourea-Induced Rat Mammary Tumorigenesis." *Journal of Agricultural and Food Chemistry*, 2010, 58: 5670-5678.
Li, Z. et al. "Synthesis and biological activity of hydroxylated derivatives of linoleic acid and conjugated linoleic acids." *Chemistry and Physics of Lipids*, Mar. 2009, 158(1): 2-9.
Rakib, A. et al. "Preventive Effect of t,t-Conjugated Linoleic Acid on 12-O-Tetradecanoylphorbol-13-acetate-Induced Inhibition of Gap Junctional Intercelleular Communication in Human Mammary Epithelial MCF-10A Cells." *Journal of Agricultural and Food Chemistry*, 2011, 59: 2-8.
Blondin, G., "Isolation, Properties, and Structural Features of Divalent Cation Ionophores Derived From Beef Heart Mitochondria," Annals of the New York Academy of Sciences 264 (1975): 98-111.
Kuklev, D.V. et al., "Synthesis of keto- and hydroxydienoic compounds from linoleic acid," Chemistry and physics of lipids 85.2 (1997): 125-134.
Tokita, M. et al., "Identification of New Geometric Isomers of Methyl Linoleate Hydroperoxide and Their Chromatographic Behavior," Bioscience, biotechnology, and biochemistry 64.5 (2000): 1044-1046.

* cited by examiner

CORIOLUS VERSICOLOR EXTRACTS, METHODS OF ISOLATING BIOLOGICALLY-ACTIVE COMPOUNDS, AND USES THEREOF

This application is a divisional application of co-pending application Ser. No. 13/804,103, filed Mar. 14, 2013; which claims the benefit of U.S. provisional Application Ser. No. 61/622,846; filed Apr. 11, 2012, both of which are incorporated herein by reference in their entirety.

BACKGROUND OF THE INVENTION

*Coriolus versicolor*, also known as *Agaricus versicolor, Boletus versicolor, Polyporus versicolor, Polystictus versicolor, Poria versicolor, Trametes versicolor*, Yun-Zhi (Chinese), Kawaratake (Japanese), and "turkey tail" (North America), belongs to the Basidiomycetes class and Polyporaceae family. It is widely distributed throughout the world, where more than 120 different strains have been identified in the wooded temperate zones of Asia, Europe, and North America.

The medicinal value of *C. versicolor* was first recorded in *Compendium of Materia Medica* (*Compendium Medica*) by Li Shi Zhen during the Ming Dynasty (1368-1644AD) in China. According to *Compendium Medica, C. versicolor* (Yun-Zhi), if consumed regularly, can invigorate vital energy, maintain one's optimal weight, promote longevity, and avoid unnecessary aging. *C. versicolor* is also believed to have protective effects on liver and spleen function, and has been used in the treatment of a variety of symptoms associated with liver dysfunction and respiratory tract infection. In China and Japan, *C. versicolor* is dried, ground, and made into tea. *C. versicolor* has not been reported to have toxic effects in long-term uses.

It is reported that *C. versicolor* has immunomodulatory, anti-tumor, antimicrobial and antiviral effects. These pharmacological effects may be largely produced by polysaccharide-peptides (PSP) such as polysaccharide Krestin (PSK).

While *C. versicolor* has a long history of empiric uses, there is still limited knowledge about the precise mechanism by which it exerts its pharmacological action. In addition, many biologically-active chemical constituents of *C. versicolor* have not been identified. A need exists for the development of more efficient and convenient extraction protocols for scaling-up the production of *C. versicolor* extracts and for the identification of its biologically-active chemical constituents for therapeutic uses.

BRIEF SUMMARY OF THE INVENTION

The subject invention provides efficient and convenient methods of isolating 9-oxo-10E, 12E-octadecadienoic acid methyl ester (9-KODE methyl ester) from *C. versicolor*. In one embodiment, the method comprises:

obtaining a *C. versicolor* extract; and isolating 9-oxo-10E, 12E-octadecadienoic acid methyl ester from the *C. versicolor* extract.

In one specific embodiment, the method of isolating 9-oxo-10E,12E-octadecadienoic acid methyl ester (9-KODE methyl ester) from *C. versicolor* comprises:

a) providing a sufficient quantity of raw material of *C. versicolor*;

b) extracting the raw material of *C. versicolor* with a polar solvent at a temperature of about 15° C. to about 30° C. to yield a *C. versicolor* extract and a residue, wherein step b) is performed once or more than once;

c) recovering the *C. versicolor* extract;

d) isolating 9-KODE methyl ester from the *C. versicolor* extract.

In one embodiment, the solvent used in step b) of the above method is a polar solvent. In a specific embodiment, the solvent is an ethanol-water mixture. In a specific embodiment, 9-KODE methyl ester is isolated from the *C. versicolor* extract using high performance liquid chromatography (HPLC).

In another embodiment, the subject invention provides therapeutic uses of compounds of formula I, and salts thereof:

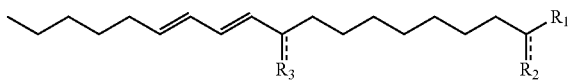

wherein

╌╌╌╌╌╌ is a double bond or a single bond;

$R_1$ is H, OH, a straight or branched chain $C_1$ to $C_4$ alkyl group (e.g., a methyl, ethyl, n-propyl, isopropyl, n-butyl, isobutyl, s-butyl or t-butyl group), or $OR_a$ wherein $R_a$ is a straight or branched chain $C_1$ to $C_4$ alkyl group; and $R_2$ is H, O, or a straight or branched chain $C_1$ to $C_4$ alkyl group; and $R_3$ is H, OH, O, halo, a straight or branched chain $C_1$ to $C_4$ alkyl group (e.g., a methyl, ethyl, n-propyl, isopropyl, n-butyl, isobutyl, s-butyl or t-butyl group), or $OR_a$ wherein $R_a$ is a straight or branched chain $C_1$ to $C_4$ alkyl group.

In one embodiment, $R_2$ is O, and $R_1$ is OH, $OCH_3$ or $OC_2H_5$. In another embodiment, $R_3$ is O or OH.

In certain specific embodiments, the compound of formula I is 9-KODE methyl ester or 9-KODE.

Advantageously, the *C. versicolor* extract and the compounds of formula I inhibit matrix metalloproteinase 3 (MMP3) expression, and can be used to inhibit the growth, invasion, and/or metastasis of cancer or tumor cells.

The subject invention further provides *C. versicolor* extracts produced by the subject extraction methods. Also provided are pharmaceutical compositions comprising a therapeutically effective amount of the subject *C. versicolor* extract, a biologically-active chemical constituent isolated from *C. versicolor*, and/or a compound of formula I, and, optionally, a pharmaceutically acceptable carrier.

The subject invention also provides methods for preventing, treating or ameliorating a disease or condition where modulation of an immune response is beneficial. In one embodiment, the method comprises administering, to a subject in need of such treatment, an effective amount of a composition comprising a therapeutically effective amount of the *C. versicolor* extract of the subject invention, a biologically-active chemical constituent isolated from *C. versicolor* (such as 9-KODE methyl ester), and/or a compound of formula I.

In one embodiment, the compositions of the subject invention can be used to treat or ameliorate cancer or tumors including, but not limited to, brain tumors, nasopharyngeal carcinoma, breast cancer, lung cancer, leukemia, lymphoma, colon cancer, liver cancer, stomach cancer, esophageal cancer, bladder cancer, and gastric cancer. In a specific embodiment, the compositions of the subject invention can be used to reduce or ameliorate metastasis or invasiveness of tumor or cancer cells.

DETAILED DESCRIPTION OF THE INVENTION

Figure 1A:
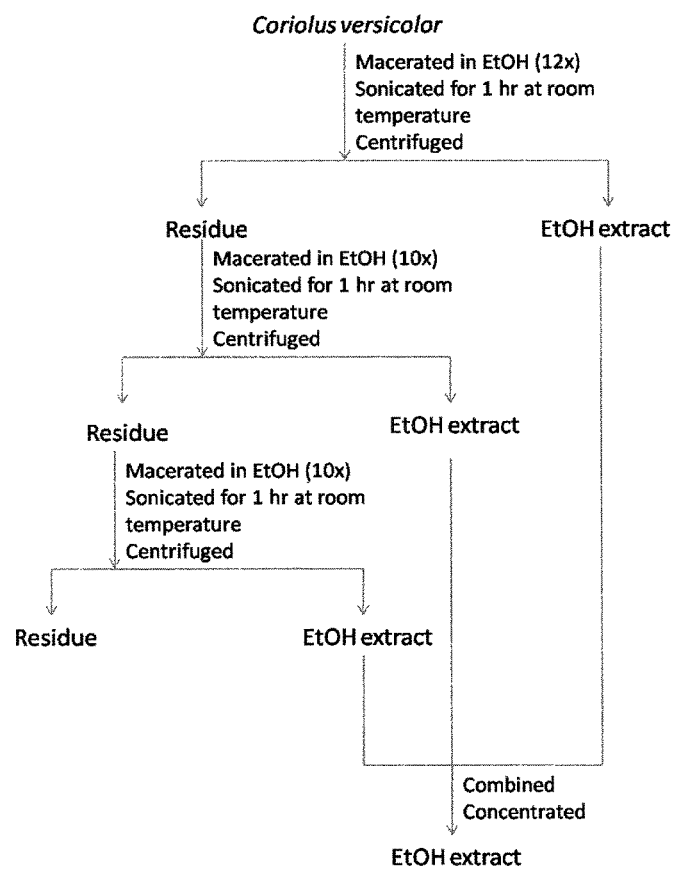
FIGS. 1A-C illustrate exemplified extraction schemes for *Coriolus versicolor*. (A) The ethanol extract of *C. versicolor* was obtained by extracting *C. versicolor* in EtOH (12-fold volume) with continuous sonication for 1 hr at room temperature. Briefly, raw materials of *C. versicolor* were macerated in 12-fold volume of ethanol with continuous sonication for 1 hr. The residues were macerated in 10-fold volume of EtOH and the extraction procedure was repeated twice. The extracts were collected, combined, and evaporated to dryness under vacuum. (B) The *C. versicolor* extract was prepared by sequential extraction, using 12×EtOH as the first solvent at room temperature, 10×50% EtOH as the second solvent under heating conditions, and 10×0.04% NaOH solution as the third solvent under heating conditions. The extracts were collected, combined, concentrated, and lyophilized. (C) The *C. versicolor* extract was prepared by sequential extraction, using 10×50% EtOH as the first solvent, and 10×0.04% NaOH solution as the second solvent. The extraction procedure was performed under heating conditions. The extracts were collected, combined, concentrated, and lyophilized.

The subject invention provides efficient and convenient methods of isolating 9-oxo-10E, 12E-octadecadienoic acid methyl ester (9-KODE methyl ester) from C. versicolor. In one embodiment, the method comprises:

obtaining a C. versicolor extract; and isolating 9-oxo-10E,12E-octadecadienoic acid methyl ester from the C. versicolor extract.

In one specific embodiment, the method of isolating 9-oxo-10E,12E-octadecadienoic acid methyl ester (9-KODE methyl ester) from C. versicolor comprises:

a) providing a sufficient quantity of raw material of C. versicolor;

b) extracting the raw material of C. versicolor with a polar solvent at a temperature of about 15° C. to about 30° C. to yield a C. versicolor extract and a residue, wherein step b) is performed once or more than once;

c) recovering the C. versicolor extract;

d) isolating 9-KODE methyl ester from the C. versicolor extract.

In one embodiment, the solvent used in step b) of the above method is a polar solvent. In a specific embodiment, the solvent is an ethanol-water mixture. In a specific embodiment, 9-KODE methyl ester is isolated from the C. versicolor extract using high performance liquid chromatography (HPLC).

The subject invention also provides efficient and convenient methods for preparing Coriolus versicolor extracts. In one preferred embodiment, the C. versicolor extract is prepared at room temperature, using water, ethanol, or a mixture of ethanol-water, as the solvent. In one embodiment, the C. versicolor extract can be further evaporated to produce solid or semi-solid compositions.

The subject invention further provides *C. versicolor* extracts produced by the subject extraction methods. Also provided are therapeutic or pharmaceutical compositions comprising a therapeutically effective amount of the subject *C. versicolor* extract, a biologically-active chemical constituent isolated from *C. versicolor* (such as 9-KODE methyl ester), and/or a compound of formula I, and, optionally, a pharmaceutically acceptable carrier. The subject invention also provides methods for preventing, treating or ameliorating a disease or condition where modulation of an immune response is beneficial. In one embodiment, the method comprises administering, to a subject in need of such treatment, an effective amount of a composition comprising the *C. versicolor* extract and compounds and compositions of the subject invention.

Specifically, the compositions of the subject invention can be used to treat or ameliorate a disease or condition, where the stimulation of IFNβ production and/or a reduction of TNF-α, IL10, and/or MMP-3 production would be beneficial.

In a preferred embodiment, the subject invention can be used to treat glioblastoma multiforme and/or nasopharyngeal carcinoma. In another embodiment, the subject invention can be used to treat bacterial, viral, and/or microbial infection. In certain embodiments, the subject invention can be used to treat infections including, but not limited to, varicella zoster, cytomegalovirus, and herpes virus 8 infections, which are common viral infections found in cancer or immunocompromised patients.

*Coriolus versicolor* Extracts and Isolated Chemical Constituents

One aspect of the subject invention provides methods for preparing *Coriolus versicolor* extracts. The subject methods can also be used to isolate biologically-active chemical constituents from *C. versicolor*. Also provided are *C. versicolor* extracts prepared in accordance with the subject invention, as well as compounds and biologically-active chemical constituents isolated from *C. versicolor*.

In addition, the subject invention provides a method of isolating 9-oxo-10E,12E-octadecadienoic acid methyl ester (9-KODE methyl ester) from *C. versicolor*. In one embodiment, the method comprises:

obtaining a *C. versicolor* extract; and isolating 9-oxo-10E,12E-octadecadienoic acid methyl ester from the *C. versicolor* extract.

In a preferred embodiment, the subject invention provides a method for preparing *C. versicolor* extract and/or for isolating biologically-active chemical constituents (such as 9-oxo-10E,12E-octadecadienoic acid methyl ester) from *C. versicolor*, comprising, consisting essentially of, or consisting of the steps of:

a) providing a sufficient quantity of raw material of *C. versicolor*;

b) extracting the raw material of *C. versicolor* with a solvent at a temperature of about 15° C. to about 30° C. to yield a *C. versicolor* extract and a residue, wherein step b) is performed once or more than once;

c) recovering the *C. versicolor* extract; and optionally, d) isolating a biologically-active chemical constituent from the *C. versicolor* extract.

In one embodiment, the solvent used in step b) of the above method is a polar solvent. Advantageously, using a polar solvent at a temperature of about 15° C. to about 30° C. facilitates the extraction of one or more biologically-active, small molecule chemical constituents, which have anti-cancer and/or anti-viral effects.

In one embodiment, the biologically-active chemical constituent isolated from *C. versicolor* is 9-oxo-10E,12E-octadecadienoic acid methyl ester. In one embodiment, the *C. versicolor* extract comprises 9-oxo-10E,12E-octadecadienoic acid methyl ester. Preferably, the raw material of *C. versicolor* is dried and ground into powder. Preferably, the *C. versicolor* extract comprises biologically-active chemical constituents, including polysaccharide-peptides (PSP) such as polysaccharide Krestin (PSK). Preferably, the raw materials are *C. versicolor* fruit bodies.

In certain embodiments, suitable solvents for the preparation of *C. versicolor* include, but are not limited to, alcohols (e.g., $C_1$-$C_8$ alcohols (e.g. methanol, ethanol, propanol, and butanol; $C_1$-$C_8$ alkyl polyols); $C_1$-$C_8$ ketones (e.g. acetone) or alkyl ketones; chloroform; acetic acid; water; and inorganic acids such as hydrochloric acid.

In one embodiment, the subject invention utilizes a ratio of *C. versicolor* to solvent (v/v) of between 1:5 and 1:20, and preferably about 1:10, 1:12, or 1:15. In preferred embodiments, the subject extraction procedure utilizes water, alcohol (e.g., ethanol), or a mixture of alcohol-water (e.g., ethanol-water), as the solvent. The alcohol-water (e.g., ethanol-water) mixture can comprise about 5%, 10%, 15%, 20%, 25%, 30%, 35%, 40%, 50%, 55%, 60%, 65%, 70%, 75%, 80%, 85%, 90%, or 95% alcohol (e.g., ethanol).

In a specific embodiment, the solvent is a water-ethanol mixture comprising 12 fold volume of 95% ethanol. It is preferred that step (b) of the extraction procedure is performed at room temperature. Step (b) can also be performed at a temperature slightly below or above room temperature. In one embodiment, step (b) is performed at a temperature of about 15° C. to about 30° C., about 18° C. to about 28° C., about 20° C. to about 28° C., or about 22° C. to about 26° C. In a specific embodiment, step (b) is performed at about 25° C.

In one embodiment, the raw material of *C. versicolor* is macerated in cold solvent, preferably at, or below, room temperature during step (b) of the extraction procedure. In one embodiment, neither the solvent nor the raw material of *C. versicolor* has been boiled or heated to a temperature of higher than 50° C., or higher than 45° C., prior to and/or during step (b) of the extraction procedure.

In one embodiment, the raw material of *C. versicolor* is mixed with solvent for at least about 15 minutes to extract the biologically-active chemical constitutes. Preferably, the extraction time is at least about 20 minutes, 30 minutes, 40 minutes, 50 minutes, 1 hour, 1.5 hours, 2 hours, 2.5 hours, 3 hours, 4 hours, or 5 hours.

Preferably, step (b) of the extraction is performed with continuous sonication. Sonication is a method that can, in some cases, improve the efficiency and shorten the extraction time for extracting compounds from the dry medicinal material. The underlying mechanism of such enhancement is the intensification of mass transfer and easier access of the solvent to the medicinal material. Thus, sonication is an expeditious, inexpensive and efficient alternative to conventional extraction techniques and, in some cases, even superior to supercritical fluid and microwave-assisted extraction.

In preferred embodiments, during step (b), the raw material of *C. versicolor* is mixed with the solvent with continuous sonication for at least about 5 minutes, 10 minutes, 15 minutes, 20 minutes, 30 minutes, 40 minutes, 50 minutes, 1 hour, 1.5 hours, 2 hours, 2.5 hours, 3 hours, 4 hours, or 5 hours. However, it has been found by the present inventors that, in certain instances, sonication may not improve the extraction yield of certain chemical constituents, which can be easily leached out from the raw medicinal materials to the solvent. In such cases, the extraction procedure is preferably performed without, or with little, sonication.

The *C. versicolor* extract can be recovered by, for example, techniques that facilitate the separation of the solid phase (e.g. residues) from the liquid phase containing the solvent extract, such as by centrifugation. The extract can be collected by, for example, filtration to remove the residues. In one embodiment, the *C. versicolor* extract may be further evaporated to produce solid or semi-solid compositions. In another embodiment, the *C. versicolor* extract may be concentrated and/or purified.

The *C. versicolor* extract and/or the biologically-active chemical constituents can be obtained via a single extraction or sequential extraction. In one embodiment, after recovering the first extract, the residues may be re-dissolved in the same solvent for further extraction. In another embodiment, the *C. versicolor* extract and/or the biologically-active chemical constituents can be obtained via sequential extraction, by extracting the solvent-extract or the residues with a different solvent each time to extract the desired biologically-active chemical constituents.

In one embodiment, the extraction method of the subject invention further comprises, consists essentially of or consists of after steps (a)-(b), the step of extracting *C. versicolor* residue with a solvent under heating conditions (such as at a temperature of about 60° C. or higher) to yield a second *C. versicolor* extract and a second residue, and optionally, isolating a biologically-active chemical constituent from the *C. versicolor* extract. In one specific embodiment, a polar solvent is used to extract *C. versicolor* residue under heating conditions.

In another embodiment, the extraction method of the subject invention further comprises, consists essentially of, or consists of after steps (a)-(b), the step of extracting *C. versicolor* residue with an aqueous alkaline solution (such as NaOH and KOH) under heating conditions (such as at a temperature of about 60° C. or higher) to yield a second *C. versicolor* extract and a second residue, and optionally, isolating a biologically-active chemical constituent from the *C. versicolor* extract. In one embodiment, the aqueous alkaline solution has a normality of 0.1N or any value lower than 0.1N, such as 0.05N, 0.02N, 0.01N, or 0.001N.

In a specific embodiment, the extraction method of the subject invention comprises:

a) providing a sufficient quantity of raw material of *C. versicolor*;

b) extracting the raw material of *C. versicolor* with a first solvent at a temperature of about 15° C. to about 30° C. to yield a first *C. versicolor* extract and a first residue;

c) extracting the first residue with a second solvent under heating conditions (such as at a temperature of about 60° C. or higher), to yield a second *C. versicolor* extract and a second residue; and d) extracting the second residue with an alkaline solution under heating conditions (such as at a temperature of about 60° C. or higher), to yield a third *C. versicolor* extract and a third residue;

e) recovering the *C. versicolor* extracts; and optionally f) isolating a biologically-active chemical constituent from the *C. versicolor* extract.

In a specific embodiment, the first and second solvents are polar solvents.

In another specific embodiment, the extraction method of the subject invention comprises:

a) providing a sufficient quantity of raw material of *C. versicolor*;

b) extracting the raw material of *C. versicolor* with a first polar solvent under heating conditions (such as at a temperature of about 60° C. or higher), to yield a first *C. versicolor* extract and a first residue; and c) extracting the first residue with an alkaline solution (such as NaOH and KOH) under heating conditions (such as at a temperature of about 60° C. or higher), to yield a second *C. versicolor* extract and a second residue;

d) extracting the *C. versicolor* extracts; and optionally e) isolating a biologically-active chemical constituent from the *C. versicolor* extract.

In one embodiment, the extraction method of the subject invention comprises, consists essentially of, or consists of:

a) providing a sufficient quantity of raw material of *Coriolus versicolor*;

b) extracting the raw material of *Coriolus versicolor* with a polar solvent to yield a *Coriolus versicolor* extract and a residue, and recovering the *Coriolus versicolor* extract, wherein step b) is performed once or more than once;

c) extracting the residue obtained in step b) with an aqueous alkaline solution to yield an aqueous extract, and recovering the aqueous extract, wherein step c) is performed once or more than once;

d) combining one or more extracts obtained from step b) and c) to yield a *Coriolus versicolor* extract; and optionally e) isolating a biologically-active chemical constituent from the *C. versicolor* extract.

In certain embodiments, the polar solvent used to extract *C. versicolor* under heating conditions comprises a $C_1$-$C_8$ alcohol (e.g. methanol, ethanol, propanol, and butanol). In a specific embodiment, the polar solvent used to extract *C. versicolor* under heating conditions is ethanol or ethanol-water mixture. In a specific embodiment, the polar solvent used to extract *C. versicolor* under heating conditions is not water.

According to the subject invention, heating can be performed at a temperature of higher than 60° C., higher than 65° C., higher than 70° C., higher than 75° C., higher than 80° C., higher than 85° C., higher than 90° C., higher than 95° C., or higher than 100° C.

Figure 1B:
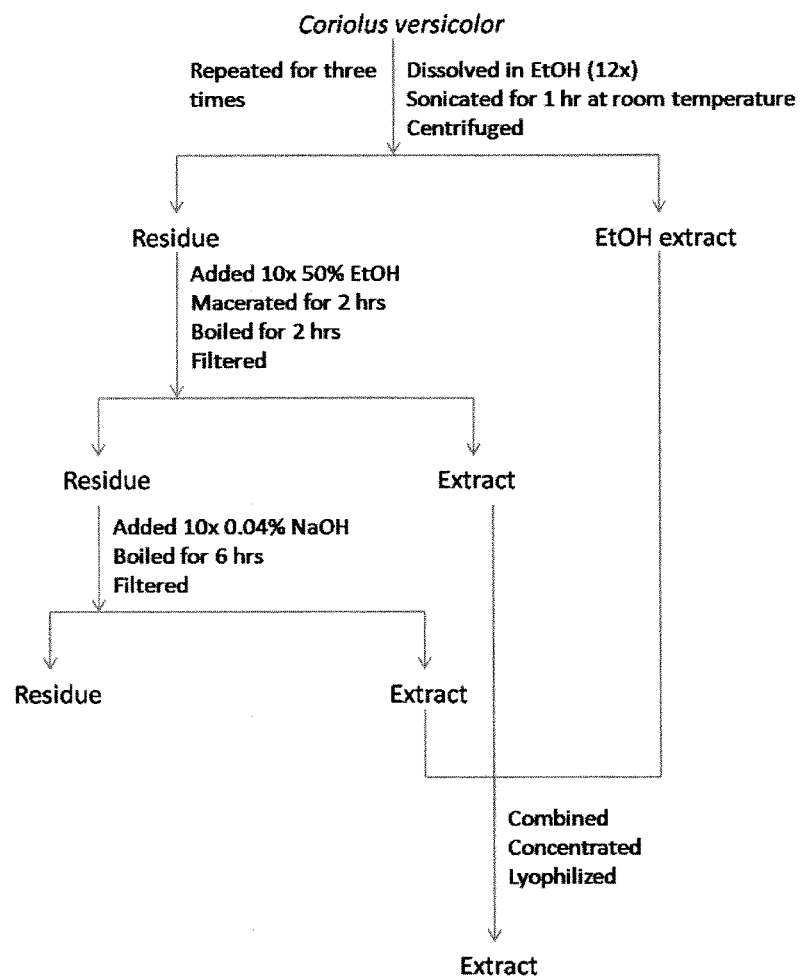
Figure 1C:
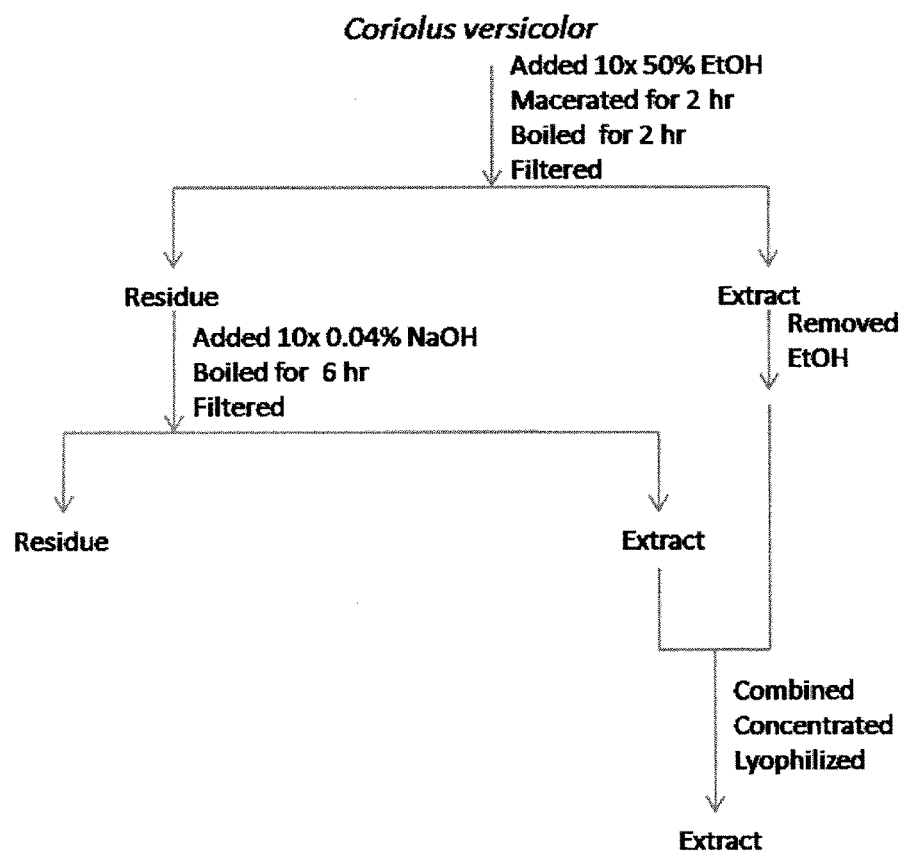

FIGS. 1A-C illustrate preferred embodiments of the extraction method of the subject invention.

Advantageously, using alkaline solution as a solvent facilitates the extraction of biologically-active, large-molecule chemical constituents, including polysaccharide-peptides (PSP) such as polysaccharide Krestin (PSK).

Figure 4:
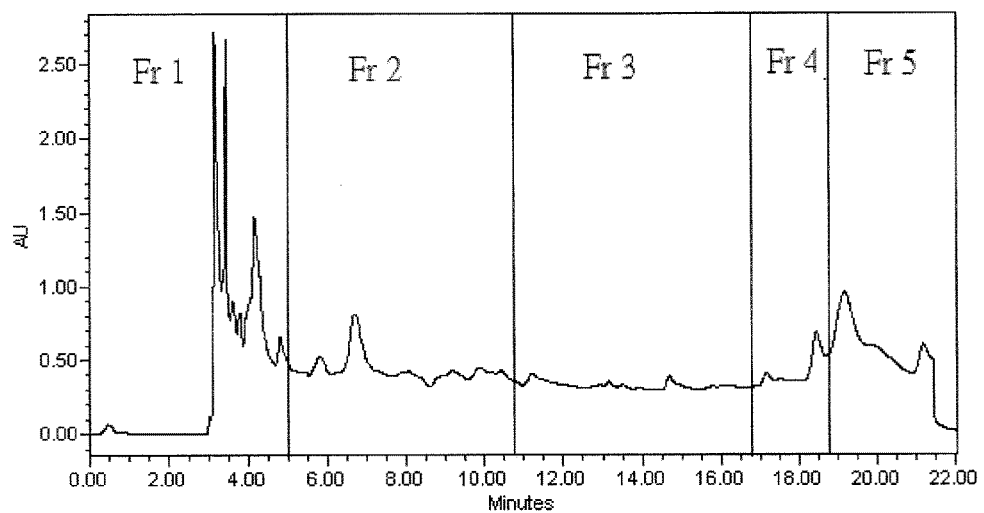
FIG. 4 shows HPLC chromatogram of *C. versicolor* ethanol extract (MPUB-EtOH) prepared using the extraction scheme as shown in FIG. 1A. The extract of MPUB-EtOH was further separated into 5 fractions using a reversed-phase column (Lichrospher 100 RP C18, EC 5 um). The flow rate was set at 1.0 ml/min and the water-acetonitrile mixture was used as the mobile phase. Peaks were detected at 210, 254, and 280 nm.

In a further embodiment, the *C. versicolor* crude extract can be fractionated or separated to yield one or more fractions that contain the desired biologically-active chemical constituents. In one embodiment, the *C. versicolor* crude extract is subject to HPLC using water-acetonitrile as the mobile phase. In certain embodiments, the water-acetonitrile is present within any ranges of water:acetonitrile of 1:100 to 100:1, including, but not limited to, water:acetonitrile of 5:95, 10:90, 20:80, 30:70, 40:60, 50:50, 60:40, 70:30, 80:20, 90:10, and 95:5. In a specific embodiment, the *C. versicolor* crude extract is subject to HPLC using the elution parameters illustrated in Table 1, thereby yielding 5 fractions as shown in FIG. 4.

In a further embodiment, the subject method comprises creating a chemical profile for the *C. versicolor* extract, by using a combination of HPLC and/or gas chromatography-mass spectrometry (GC-MS). In one embodiment, the method comprises: subjecting the extract to a HPLC, eluting the extract, and creating a chemical profile for the extract following HPLC. In another embodiment, the method comprises: subjecting the extract to a gas chromatography-mass spectrometry and creating a chromatographic/spectrometric profile for the extract.

Figure 2A:
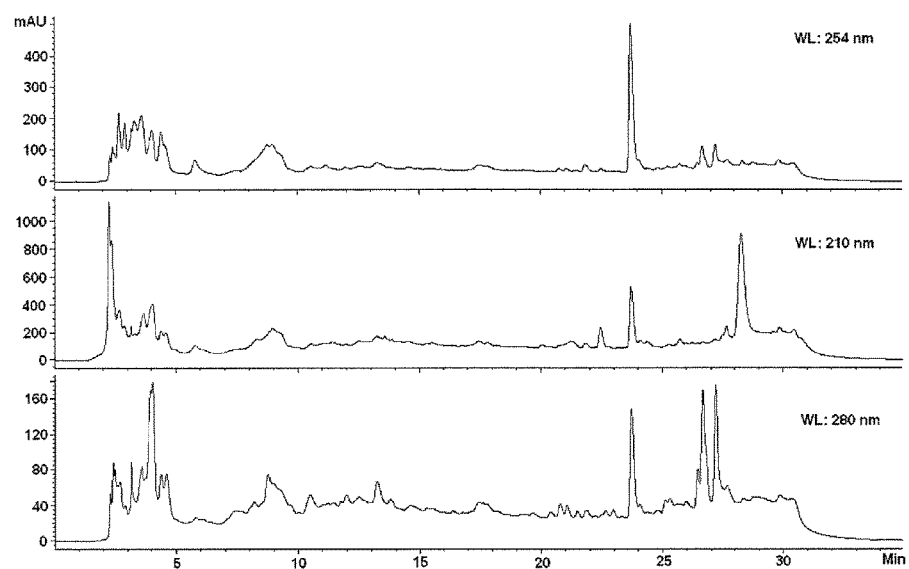
FIGS. 2A-C show high performance liquid chromatography (HPLC) chromatograms of *C. versicolor* ethanol extract prepared using the extraction schemes as shown in FIG. 1A, 1B, or by macerating the raw materials of *C. versicolor* in ethanol for 18 hrs. The *C. versicolor* ethanol extract was subject to HPLC by using Agilent 1200 series HPLC system with a column packed with ODS-bonded silica gel (Lichrospher 100 RP C18, EC 5 um). The flow rate was set at 1.0 ml/min and the water-acetonitrile mixture was used as the mobile phase. Peaks were detected at 210, 254, and 280 nm. (A) HPLC chromatograms of *C. versicolor* extract, which was extracted with ethanol under continuous sonication for 1 hr. The extraction procedure was repeated twice. (B) HPLC chromatograms of *C. versicolor* extract, which was extracted by maceration in ethanol for 18 hrs. (C) HPLC chromatograms of *C. versicolor* extract, which was extracted using the extraction scheme as shown in FIG. 1B. Briefly, *C. versicolor* was extracted with ethanol at room temperature and then extracted with 50% ethanol under heating conditions.
Figure 2B:
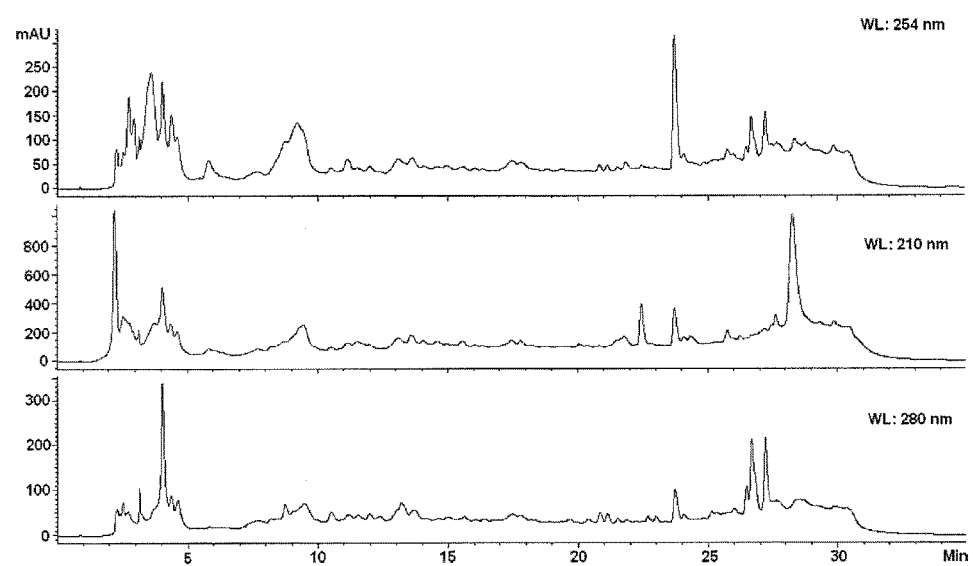
Figure 2C:
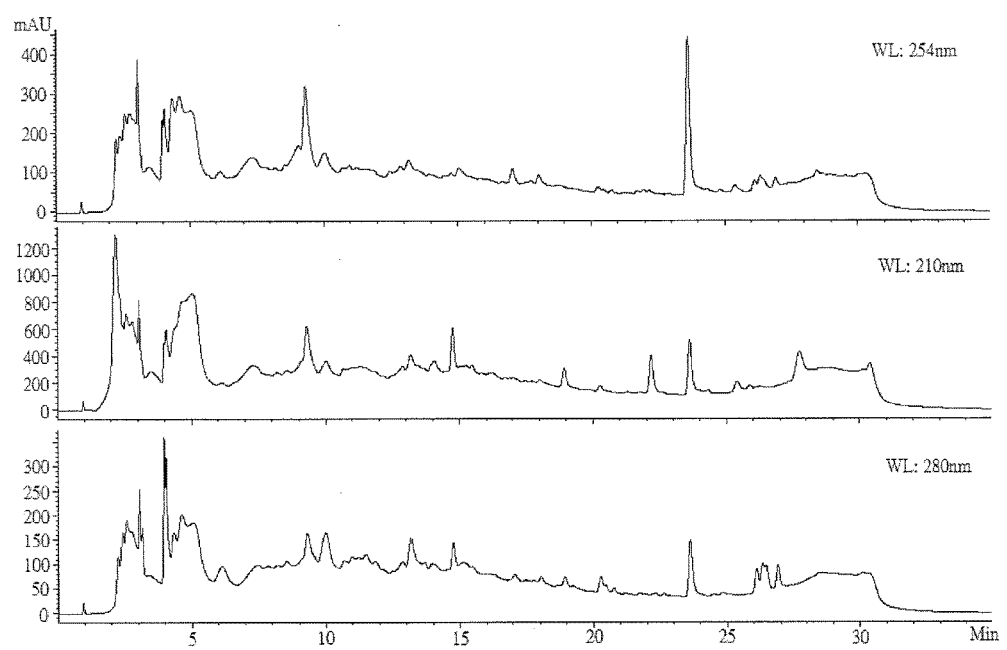
Figure 3A:
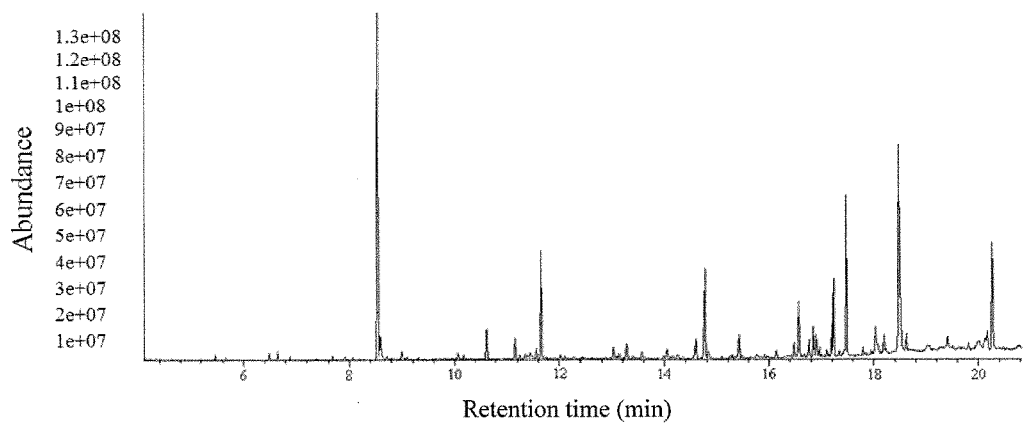
FIG. 3A-B show gas chromatography (GC) total ion chromatogram of *C. versicolor* ethanol extract prepared using the extraction scheme as shown in FIG. 1A or by macerating the raw materials of *C. versicolor* in ethanol for 18 hrs. The extract was mixed with pyridine and a derivatizing agent BSTFA [N,O-bis(trimethylsilyl) trifloroacetamide] at 70° C. for 2 hrs. The resulting mixture was analyzed by gas chromatography mass spectrometry (GC-MS) with a HP-5MS column (30 m×250 um×0.25 um). The initial oven temperature was maintained at 70° C. for 1 min, increased to 180° C. at a rate of 10° C. per min, maintained at 180° C. for 2 min, increased to 280° C. at a rate of 10° C. per min, and maintained at 280° C. for 3 min. The injector temperature was set at 275° C. Helium at a flow rate of 1 ml/min was used as the carrier gas. (A) Gas chromatography (GC) total ion chromatogram of *C. versicolor* extract, which was extracted with ethanol under continuous sonication for 1 hr. The extraction procedure was repeated twice. (B) Gas chromatography (GC) total ion chromatogram of *C. versicolor* extract, which was extracted by maceration in ethanol for 18 hrs.
Figure 3B:
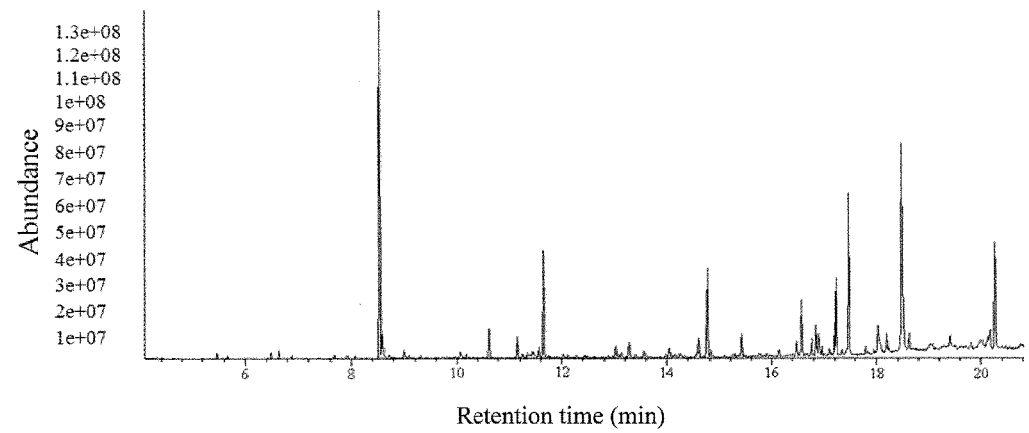

The subject invention further provides *C. versicolor* extracts produced by the subject extraction methods. In a specific embodiment, the *C. versicolor* extract has a high performance liquid chromatography (HPLC) profile as shown in FIG. 2A, 2B, 2C, or any of Fractions 1-5 as shown in FIG. 4; and/or a gas chromatography-mass spectrometry (GC-MS) profile as shown in FIG. 3A or 3B.

The term "consisting essentially of," as used herein, limits the scope of the invention to the specified steps and those that do not materially affect the basic and novel characteristic(s) of the subject invention, i.e., a method for preparing *C. versicolor* extract and/or for isolating biologically-active chemical constituents from *C. versicolor*. For instance, by using "consisting essentially of," the method for preparing *C. versicolor* extract does not contain any unspecified steps of extracting or contacting *C. versicolor*, for example, additional step(s) of extracting or contacting *C. versicolor* with unspecified solvent(s), or extracting *C. versicolor* under condition(s) (e.g., temperature) different from the specified condition. Also, by using the term "consisting essentially of," the process may comprise steps that do not materially affect the extraction of biologically-active chemical constituents from *C. versicolor* including collecting or recovering the *C. versicolor* extract; concentrating the *C. versicolor* extract; combining multiple *C. versicolor* extracts into a single composition; lyophilizing or drying the *C. versicolor* extract into a solid or semi-solid composition; formulating the *C. versicolor* extract into a pharmaceutical composition such as solutions, suspensions, tablets, capsules, granules, powders, decoctions, and tinctures; mixing the *C. versicolor* extract with pharmaceutically-acceptable carriers, excipients, flavoring agents, buffering agents, and/or emulsifying agents; and packaging the *C. versicolor* extract.

Compounds

In another aspect, the subject invention pertains to 9-oxo-10E, 12E-octadecadienoic acid methyl ester (9-KODE methyl ester) and related compounds. In one embodiment, the compound useful according to the subject invention has a chemical structure as shown in formula I:

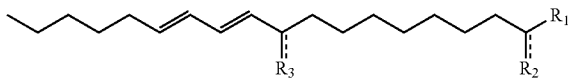

wherein
⚌⚌⚌ is a double bond or a single bond;
$R_1$ is H, OH, a straight or branched chain $C_1$ to $C_4$ alkyl group (e.g., a methyl, ethyl, n-propyl, isopropyl, n-butyl, isobutyl, s-butyl or t-butyl group), or $OR_a$ wherein $R_a$ is a straight or branched chain $C_1$ to $C_4$ alkyl group; and
$R_2$ is H, O, or a straight or branched chain $C_1$ to $C_4$ alkyl group; and
$R_3$ is H, OH, O, halo, a straight or branched chain $C_1$ to $C_4$ alkyl group (e.g., a methyl, ethyl, n-propyl, isopropyl, n-butyl, isobutyl, s-butyl or t-butyl group), or $OR_a$ wherein $R_a$ is a straight or branched chain $C_1$ to $C_4$ alkyl group.

In one embodiment, $R_2$ is O, and $R_1$ is OH, $OCH_3$ or $OC_2H_5$. In another embodiment, $R_3$ is O or OH.

In one embodiment, the alkyl groups of Formula I can be substituted or unsubstituted.

The term "alkyl," as used herein, refers to a linear or branched saturated monovalent radical that contains carbon and hydrogen. Representative examples of alkyl groups include, but are not limited to, methyl, ethyl, propyl, 2-propyl, n-butyl, iso-butyl, and tert-butyl.

The term "halo" means fluoro, chloro, bromo, and iodo.
The term "hydroxy" means the radical —OH.
The term "substituted," as used herein, refers to that at least one hydrogen atom of a compound or chemical moiety is replaced with a second chemical moiety. Non-limiting examples of substituents are those found in the exemplary compounds and embodiments disclosed herein, as well as halogen; alkyl; alkenyl; alkynyl; hydroxy; alkoxyl; amino; haloalkyl (e.g., trifluoromethyl); and —COOH. All chemical groups disclosed herein can be substituted, unless it is specified otherwise. For example, "substituted" alkyl, alkenyl, or alkynyl moieties described herein are moieties that are substituted with a second chemical moiety such as a hydrocarbyl moiety, halo, alkoxy, and —COOH. Substituted alkyl groups include, but are not limited to, haloalkyl, hydroxyalkyl, carboxylalkyl, and aminoalkyl.

In one embodiment, a compound of formula I useful in accordance with the present invention is 9-oxo-10E, 12E-octadecadienoic acid methyl ester (9-KODE methyl ester), having the following structure:

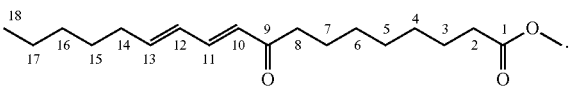

In another embodiment, a compound of formula I useful in accordance with the present invention is 9-oxo-10E, 12E-octadecadienoic acid (9-KODE).

In certain embodiments, the present invention pertains to the use of isolated or substantially pure compounds represented by formula I. The term "substantially pure," as used herein, refers to more than 99% pure.

Advantageously, the compounds of formula I inhibit TNF-α induced matrix metalloproteinase 3 (MMP3) expression, and can be used to inhibit the growth, invasion, and/or metastasis of cancer or tumor cells.

The compounds of the present invention can be isolated from plants or can be synthesized using methods known in the art. See Kuklev et al. (1997) and Andreou et al. (2009).

As used herein, "isolated" refers to compounds that have been removed from any environment in which they may exist in nature. For example, an isolated compound would not refer to the compound as it exists in plants from which compound can be isolated. In preferred embodiments, the compounds of the present invention are at least 75% pure, preferably at least 90% pure, more preferably are more than 95% pure, and most preferably are more than 99% pure (substantially pure).

The present invention further embodies stereoisomers of the compounds of formula (I). The term "stereoisomer" encompasses all enantiomerically/stereomerically pure and enantiomerically/stereomerically enriched compounds disclosed herein.

In one embodiment, the present invention pertains to enantiomeric forms of the compounds of formula (I). The enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least about 99% enantiomeric excess.

Uses for Modulation of Immune Responses and Treatment of Cancer

Another aspect of the subject invention provides therapeutic uses of the *Coriolus versicolor* extracts, biologically-active substituents isolated from *C. versicolor* (e.g., 9-KODE methyl ester), and/or compounds of formula I and salts thereof, as well as therapeutic compositions comprising one or more of the aforementioned ingredients, for modulating immune responses and for treatment of cancer.

Advantageously, the *C. versicolor* extracts of the subject invention and the compounds of formula I stimulate protective immune responses while suppressing unwanted immune responses that can cause disease. For instance, the *C. versicolor* extracts and the compounds of formula I can restore or improve depressed immune system function, which is caused by, for example, the administration of anti-cancer agents.

In another embodiment, the *C. versicolor* extracts and the compounds of formula I can stimulate protective immune responses that defend against viral, bacterial, and/or microbial infection.

In addition, the *C. versicolor* extracts and the compounds of formula I of the subject invention can suppress unwanted immune responses, such as the production of TNF-α and its induction of metalloproteinase production, which are utilized by certain tumor cells to promote metastasis.

Specifically, it is now discovered by the present inventors that the *C. versicolor* extract of the subject invention and the compounds of formula I reduce the production of TNF-α, a pro-inflammatory mediator that plays a critical role in the acute-phase immune response against pathogenic infection and tumorigenesis. TNF-α also induces the production of matrix metalloproteinases (MMPs) and MMP family members, which degrade extracellular matrix proteins. However, certain tumor cells (such as glioblastomas, nasopharyngeal carcinomas, breast carcinoma, lung carcinoma, prostate cancer, and colon carcinoma) have developed resistance to the cytotoxic effects of TNF-α. As a result, these tumor cells utilize the induction of MMP by TNF-α to invade neighboring tissues as well as organs located in distant parts of the body.

Advantageously, the *C. versicolor* extract of the subject invention and the compounds of formula I inhibit TNF-α production in tumor cells and, thus, is particularly useful for preventing or reducing the metastatic spread of malignant tumor cells (such as glioblastoma, nasopharyngeal carcinoma, breast carcinoma, lung carcinoma, prostate cancer cells, and colon carcinoma) that are resistant to TNF-α.

In addition, it is now discovered by the present inventors that *C. versicolor* reduces the production of IL-10, an anti-inflammatory cytokine that down-regulates the expression of pro-inflammatory cytokines. It is also discovered by the present inventors that *C. versicolor* enhances the production of IFN-β, which stimulates the acute-phase immune response against pathogenic invasion.

In one embodiment, the subject invention provides a method for preventing, treating, or ameliorating a disease or condition where modulation of immune responses would be beneficial. The method comprises administering, to a subject in need of such treatment, an effective amount of a composition comprising the *C. versicolor* extract of the subject invention, a biologically-active substituent isolated from *C. versicolor* (e.g., 9-KODE methyl ester), and/or a compound of formula I.

Specifically, the compositions of the subject invention can be used to treat or ameliorate a disease or condition, where the stimulation of IFNβ production and/or reduction of the production or level of TNF-α, MMP3, and/or IL-10 would be beneficial.

The term "subject," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; domesticated animals such as dogs, cats, horses, cattle, pigs, sheep, goats, chickens; and other animals such as mice, rats, guinea pigs, and hamsters.

In one embodiment, the subject is diagnosed as having a condition that can be treated in accordance with the present invention. In certain embodiments, the subject in need of treatment is diagnosed as having cancer or tumors including, but not limited to, glioblastoma, brain tumors, nasopharyngeal carcinoma, breast cancer, leukemia, lymphoma, colon cancer, liver cancer, stomach cancer, esophageal cancer, bladder cancer, lung cancer, prostate cancer, and gastric cancer. In one embodiment, the subject in need of treatment has metastatic cancer. In one embodiment, the subject in need of treat has viral, bacterial, and/or microbial infection.

In one embodiment, the present invention comprises the step of diagnosing whether the subject has a condition that can be treated in accordance with the present invention.

In certain embodiments, the compounds and compositions of the present invention can be used to treat benign and/or malignant tumors.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition.

The term "prevention" or any grammatical variation thereof (e.g., prevent, preventing, and prevention etc.), as used herein, includes but is not limited to, delaying the onset of symptoms, preventing relapse to a disease, increasing latency between symptomatic episodes, or a combination thereof. Prevention, as used herein, does not require the complete absence of symptoms.

The term "effective amount," as used herein, refers to an amount that is capable of treating or ameliorating a disease or condition or otherwise capable of producing an intended therapeutic effect. In certain embodiments, the effective amount enables at least 5%, 10%, 15%, 20%, 25%, 30%, 35%, 40%, 45%, 50%, 60%, 70%, 80%, 90%, or 100% reduction in the production or level of TNF-α, MMP3, and/or IL-10. In certain embodiments, the effective amount enables at least 5%, 10%, 15%, 20%, 25%, 30%, 35%, 40%, 45%, 50%, 60%, 70%, 80%, 90%, or 100% increase in IFNβ level or production.

In one embodiment, the compounds and compositions of the subject invention can be used to treat or ameliorate cancer or tumors including, but not limited to, glioblastoma, brain tumors, nasopharyngeal carcinoma, breast cancer, leukemia, lymphoma, colon cancer, liver cancer, stomach cancer, esophageal cancer, bladder cancer, and gastric cancer. In a preferred embodiment, the subject invention can be used to prevent or reduce the metastatic spread of tumor cells, particularly those tumor cells that become resistant to the cytotoxic effects of TNF-α. In a specific embodiment, the subject invention can be used to treat glioblastoma multiforme, breast carcinoma, lung carcinoma, prostate cancer, colon carcinoma and/or nasopharyngeal carcinoma. In a further specific embodiment, the subject invention can be used to prevent or reduce the metastatic spread of glioblastoma multiforme, breast carcinoma, lung carcinoma, prostate cancer, colon carcinoma, and/or nasopharyngeal carcinoma.

In one embodiment, the subject invention can be used to strengthen the immune system and/or restore or improve immune system function. In a specific embodiment, the compositions of the subject invention can be used to treat or ameliorate the immuno-suppressive effects of chemotherapy and/or radiation therapy. In one embodiment, the composition of the subject invention is administered before, during, and/or after the administration of a chemotherapeutic agent to counteract the depressive effects of the chemotherapeutic agent on the immune system.

In addition, the compositions of the subject invention can be used to prevent, treat or ameliorate bacterial, viral, fungal, protozoan, and/or other microbial or pathogenic infections. Advantageously, the compositions of the subject invention modulate and/or strengthen immune system function in response to pathogenic infection.

In one embodiment, the compositions of the subject invention can be used to treat or ameliorate viral infection, such as for example, infection by human immunodeficiency virus (HIV), influenza A virus, influenza B virus, hepatitis A virus, hepatitis B virus, hepatitis C virus, herpes simplex virus (HSV), varicella zoster (shingles), herpes virus-8, cytomegalovirus, human T-lymphotropic virus Type I (HTLV-1), bovine leukemia virus (BLV), Epstein-Barr virus, and coronavirus.

In certain embodiments, the compositions of the subject invention can be used to treat or ameliorate fungal infections including, but not limited to, infection by *Candida* and *Aspergillus* species; bacterial infections including, but not limited to, infection by mycobacteria (such as *M. tuberculosis*), *Staphylococcus aureus*, *Streptococcus pyogenes*, *Streptococcus pneumoniae*, *Escherichii coli*, *Listeria monocytogenes*, and *L. amazonensis*; and protozoan infections including, but not limited to, infection by *Pneumocystis* and *Toxoplasma* species.

In one embodiment, the compositions of the subject invention can be used to treat liver dysfunction, respiratory tract infection, and bronchitis.

Therapeutic Compositions and Formulations

The subject invention provides for therapeutic or pharmaceutical compositions comprising a therapeutically effective amount of the *Coriolus versicolor* extract, biologically-active chemical constituents and/or compounds of the subject invention and, optionally, a pharmaceutically acceptable carrier. The subject invention also provides therapeutic or pharmaceutical compositions comprising biologically-active compounds or chemical constituents isolated from *C. versicolor* in accordance with the subject invention. The present invention also embodies dietary supplements and health food or drink formulations comprising the *C. versicolor* extract of the invention.

The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents. These compositions can take the form of solutions, suspensions, emulsion, tablets, capsules, granules, powders, sustained-release formulations and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

The therapeutic or pharmaceutical compositions of the invention can be formulated as neutral or salt forms. Pharmaceutically acceptable salts include, but are not limited to, salts formed with hydrochloric, phosphoric, acetic, oxalic, tartaric acids, sodium, potassium, ammonium, calcium, ferric hydroxides, etc.

The invention also provides a pharmaceutical pack or kit comprising one or more containers filled with one or more of the ingredients, e.g., compound, carrier, of the pharmaceutical compositions of the invention.

The compositions of the subject invention can also be formulated consistent with traditional Chinese medicine practices. The composition and dosage of the formulation that are effective in the treatment of a particular disease, condition or disorder will depend on the nature of the disease, condition or disorder by standard clinical techniques.

The traditional Chinese medicine in prescription amounts can be readily made into any form of drug, suitable for administering to humans or animals. Suitable forms include, for example, tinctures, decoctions, and dry extracts. These can be taken orally, applied through venous injection or mucous membranes. The active ingredient can also be formulated into capsules, powder, pallets, pastille, suppositories, oral solutions, pasteurized gastroenteric suspension injections, small or large amounts of injection, frozen powder injections, pasteurized powder injections and the like. All of the above-mentioned methods are known to people skilled in the art, described in books and commonly used by practitioners of herbal medicine.

A tincture is prepared by suspending raw medicinal materials (e.g. herbs and fungus) in a solution of alcohol, such as, for example, wine or liquor. After a period of suspension, the liquid (the alcohol solution) may be administered, for example, two or three times a day, one teaspoon each time.

An extract is a concentrated preparation of the essential constituents of a medicinal raw material. Typically, the essential constituents are extracted from the raw medicinal materials (e.g. herbs and fungus) by suspending the raw medicinal materials in an appropriate choice of solvent, typically, water, ethanol/water mixture, methanol, butanol, iso-butanol, acetone, hexane, petroleum ether or other organic solvents. The extracting process may be further facilitated by means of maceration, percolation, repercolation, counter-current extraction, turbo-extraction, or by carbon-dioxide hypercritical (temperature/pressure) extraction. After filtration to rid of herb debris, the extracting solution may be further evaporated and thus concentrated to yield a soft extract (extractum spissum) and/or eventually a dried extract, extractum siccum, by means of spray drying, vacuum oven drying, fluid-bed drying or freeze-drying. The soft extract or dried extract may be further dissolved in a suitable liquid to a desired concentration for administering or processed into a form such as pills, capsules, injections, etc.

Routes of Administration

The compounds and compositions of the subject invention can be administered to the subject being treated by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject. In preferred embodiments, the compounds and compositions of the subject invention are administered to a subject by oral administration.

The amount of the therapeutic or pharmaceutical composition of the invention which is effective in the treatment of a particular disease, condition or disorder will depend on the route of administration, and the seriousness of the disease, condition or disorder, and should be decided according to the judgment of the practitioner and each patient's circumstances. In general, the dosage ranges from about 0.001 mg/kg to about 3 g/kg.

For instance, suitable unit dosages may be between about 0.01 to about 500 mg, about 0.01 to about 400 mg, about 0.01 to about 300 mg, about 0.01 to about 200 mg, about 0.01 to about 100 mg, about 0.01 to about 50 mg, about 0.01 to about 30 mg, about 0.01 to about 20 mg, about 0.01 to about 10 mg, about 0.01 to about 5 mg, about 0.01 to about 3 mg about, 0.01 to about 1 mg, or about 0.01 to about 0.5 mg. Such a unit dose may be administered more than once a day, e.g. two or three times a day.

The amount of active ingredient that may be combined with the carrier materials to produce a single dosage form will vary, depending on the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

Once improvement of the patient's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems.

Materials and Methods

Cell Cultures for Bioassays

Primary human blood macrophages and human leukemic monocyte lymphoma cells (U937) were used in bioassays examining the effects of *C. versicolor* extract on the immune system. Blood mononuclear cells were isolated from blood samples of healthy donors (Hong Kong Red Cross Blood Transfusion Service) by Ficoll-Paque centrifugation and purified by the adherence method as described previously (Yang et al. (2009); Cheng et al. (2009)).

Briefly, blood samples were centrifuged at 3000 rpm for 15 min and were separated into plasma and cell layers. The cell layer was diluted with phosphate buffered saline (PBS) in a ratio of 1:1. The diluted cells were slowly overlaid on Ficoll (GE Healthcare) and centrifuged at 2300 rpm for 20 min for separation of mononuclear cells from erythrocytes. The mononuclear cell layer was removed and washed with RPMI 1640 medium (Gibco) until the supernatant was clear.

The cell pellet was resuspended in RPMI 1640 supplemented with 5% autologous plasma, 1% penicillin and streptomycin (Gibco). The suspension was plated onto a petri dish and incubated at 37° C. for 1 h for monocyte adherence. Following washings with RPMI 1640 and overnight incubation, the adherent monocytes were detached by cold RPMI 1640 containing 5 mM EDTA.

The monocytes were seeded onto 24-well tissue culture plates at a density of $0.5 \times 10^6$ cells/well and incubated with RPMI 1640 supplemented with 5% autologous plasma, 1% penicillin and streptomycin. Differentiated macrophages were obtained after 14 days of in vitro culture as described in our previous reports (Yang et al. (2009); Lee et al. (2009)).

Mouse macrophages (RAW 264.7) and human neuroblast cells (SKNSH) obtained from American Type Culture Collection were maintained in cultures for use in nitric oxide assays and herpes simplex virus infection assays, respectively.

Real-Time Reverse Transcription-Polymerase Chain Reaction for Analysis of mRNA

Total RNA extraction was performed by using TRIzol reagent (Invitrogen) according to the manufacturer's instructions. Total RNA was treated with DNase and then reverse transcribed by Superscript II reverse transcriptase (Invitrogen) with oligo (dT) primers. The mRNA levels of cytokines were assayed by using TaqMan gene expression assays (Applied Biosystems) as described in our previous reports (Yang et al. (2009); Cheng et al. (2009); Law et al. (2009); Lee et al. (2009)).

Enzyme-Linked Immunosorbent Assay for Analysis of Cytokines

Protein levels of cytokines in the cell culture supernatants were measured by enzyme-linked immunosorbent assay (ELISA) using commercially available assay kits (R&D Systems) (Yang et al. (2009); Cheng et al. (2009); Law et al. (2009); Lee et al. (2009)). Each sample was assayed in duplicates.

Preparation of Ethanol (EtOH) Extract of *C. versicolor*

Authenticated samples of the herb *C. versicolor* were obtained from PuraPharm International (Hong Kong, China). Four batches of *C. versicolor* (R08PUB, R09PUB, R10PUB and R11PUB) were macerated separately in 12-fold volume of 95% EtOH and then extracted for 1 hr with continuous sonication or macerated for 24 hr at room temperature. The extraction procedure was repeated twice. The extracts were combined and evaporated to dryness under vacuum.

Isolation and Identification of Compound Cove-1 from R10PUB

R10PUB was separated using Sep-Pak C18 cartridges (Waters, Ireland). The column was eluted using the following solvent systems: ACN/$H_2O$ (5:95), ACN/$H_2O$ (10:90), ACN/$H_2O$ (15:85), ACN/$H_2O$ (30:70), ACN/$H_2O$ (50:50) and ACN (100%). Using a bioassay-guided fractionation scheme, the active fraction eluted with 100% ACN (R10PUB-S6) was further separated using the Sep-Pak C18 cartridges. The column was eluted using the following solvent systems: ACN/$H_2O$ (50:50), ACN/$H_2O$ (60:40), ACN/$H_2O$ (70:30), ACN/$H_2O$ (80:20), ACN/$H_2O$ (90:10) and ACN (100%). The resulting bioactive fraction eluted with 80% ACN (R10PUB-S6-4) was purified using HPLC equipped with a reversed phase 5 μm $C_{18}$ Eclipse (4.6×250 mm) column. Compounds were eluted using a gradient elution from 20% ACN to 90% ACN at a flow rate of 1.0 ml/min and all the measurements were performed at room temperature. Peak detection was achieved using an Agilent 1200 series of fast scanning photodiode array detector set at 210, 254, and 280 nm. By repeating the purification process using HPLC, a pure compound (compound Cove-1) (3.3 mg) with purity more than 95% was obtained.

Structure Elucidation of the Molecular Structure

The 1D [$^1$H (500 MHz), $^{13}$C (125 MHz) and Dept 135°] and 2D ($^1$H-$^1$H COSY and HSQC) were acquired on Bruker 500 MHz DRX NMR spectrometer. The chemical shift were referenced with respect to an internal standard $(CH_3)_4Si$ (0 ppm) for solutions in methanol-d. EI-MS was performed on an Agilent GC-mass spectrometer (GC: Agilent, 7890A, MS: Agilent, 5975C) equipped with a HP-5MS column (30 m×250 μm×0.25 μm). One microliter of the sample was injected. Helium was used as the carrier gas in a flow of 1 ml/min. The oven temperature was started at 70° C. for 1 min, and then increased to 280° C. at a rate of 10° C./min and held for 3 min. The interface temperature was 250° C., ion source temperature was 230° C., and electron impact ionization (EI) was at 200 eV. Mass spectra were analyzed in the range of 50-350 atom mass units (amu) for a run time of 25 min. The G1701EA chemstation (Agilent, Santa Clara, Calif.) was used to perform MS data analysis.

Real-Time Reverse Transcription-Polymerase Chain Reaction for Analysis of mRNA

Glioblastoma (T98G, brain cells) cells were pretreated with different batches of ethanol extract or purified compounds of C. versicolor for 18 hr, and then treated with recombinant human TNF-α (10 ng/ml) for another 3 hr. Total RNA extraction was performed by TRIzol reagent (Invitrogen) according to the manufacturer's instructions. Total RNA was reverse transcribed by Superscript II reverse transcriptase (Invitrogen) with oligo (dT) primers. MMP-3 mRNA levels were analyzed by TaqMan Gene Expression Assays (Applied Biosystems). All data were plotted as mean values±SD of at least 3 independent experiments. * P<0.05, or ** P<0.01 was considered statistically significant.

Enzyme-Linked Immunosorbent Assay for Analysis of MMP-3

T98G cells were pretreated with different batches of ethanol extract of C. versicolor for 18 hr, and then treated with recombinant human TNF-α (10 ng/ml) for another 24 hr. Protein levels of MMP-3 in the cell culture supernatants were analyzed by enzyme-linked immunosorbent assays (ELISA) using commercially available assay kits (R&D Systems). All data were plotted as mean values±SD of at least 3 independent experiments. * P<0.05 or, ** P<0.01 was considered statistically significant.

MTT Assay

T98G cells were incubated with different batches of ethanol extract or purified compounds of C. versicolor for 48 hr. After treatment, MTT (3-[4,5-dimethylthiazol-2-yl]-2,5-di-phenyltetrazolim bromide) (Sigma) was added to the medium at a final concentration of 1 mg/ml and followed by 2 hr incubation at 37° C. MTT formazan formed was then dissolved in 200 μl of isopropanol and the absorbance of the supernatant was measured at 570 nm using a 96-well microplate reader. All data were plotted as mean values±SD of at least 3 independent experiments.

Tumor Cell Invasion Assay

Cell invasiveness was studied using BD BioCoat™ Matrigel™ Invasion Chamber (BD Biosciences). T98G cells suspended in MEM containing 1% FBS, 1% penicillin-streptomycin and 1% sodium pyruvate were seeded overnight on top of gel in each chamber. Bicarbonate based culture medium was added into the bottom wells of the plate. After incubation, the cells were treated with ethanol extract of C. versicolor/Cove-1 for 18 hr. The chambers were then transferred to a new plate with each well containing MEM supplemented with 10% FBS. Cells were allowed to invade through the matrices at 37° C. for another 24 hr. After the invasion assay, invaded cells on the lower surface of the chamber were fixed with 100% methanol for 2 min, and stained with Crystal Violet. The number of invading cells was quantified by counting under a light microscope. All data were plotted as mean values±SD of at least 3 independent experiments. ** P<0.01 was considered statistically significant.

EXAMPLES

Following are examples that illustrate embodiments for practicing the invention. These examples should not be construed as limiting. All solvent mixture proportions are by volume unless otherwise noted.

Example 1—Preparation of Coriolus versicolor Extract

This Example illustrates preferred extraction schemes for preparing C. versicolor extracts.

FIG. 1A illustrates one embodiment of the extraction scheme. Briefly, raw materials of C. versicolor were macerated in 12-fold volume of EtOH, extracted for 1 hr with continuous sonication at room temperature, and centrifuged to yield ethanol extract and residues. The residues were macerated in 10-fold volume of EtOH and the extraction procedure was repeated twice as shown in FIG. 1A. The extracts were collected, combined, and evaporated to dryness under vacuum to produce granules comprising C. versicolor ethanol extract.

In an embodiment, raw materials of C. versicolor were macerated in ethanol for 18 hrs, and centrifuged to yield the ethanol extract and residues.

In an embodiment, milli-Q water is used as the solvent for preparing C. versicolor water extract. Briefly, raw materials of C. versicolor were macerated in 15-fold volume of milli-Q water, extracted for 30 min with continuous sonication at room temperature, and centrifuged to yield water extract and residues. The residues were re-dissolved in 10-fold volume of water and the extraction procedure was repeated twice. The water extract was collected, combined and evaporated to dryness under vacuum to produce granules comprising *C. versicolor* water extract.

In order to facilitate the extraction of bioactive large molecules, including polysaccharide-peptides (PSP) such as PSK and other bioactive small molecules, raw materials of *C. versicolor* or *C. versicolor* residues were further extracted with alkaline solution (e.g., NaOH, KOH).

FIG. 1B shows another embodiment of the extraction scheme. Briefly, raw materials of *C. versicolor* were macerated in 12-fold volume of ethanol with continuous sonication for 1 hr at room temperature. After centrifugation, the first extract and the first residue were obtained. This procedure was repeated twice. The first residue was macerated in 10-fold volume of 50% ethanol for 2 hrs at room temperature. The ethanol-macerated residue was then boiled for another 2 hrs. Insoluble substances were separated from supernatant by filtration, to yield a second residue and a second extract. The second residue was added into 10×0.04% NaOH and boiled for 6 hrs. Insoluble substances were separated from supernatant by filtration, to yield a third residue and a third extract. The extracts were collected, combined, and lyophilized.

FIG. 1C shows another embodiment of the extraction scheme. Briefly, raw materials of *C. versicolor* were macerated in 10-fold 50% ethanol for 2 hrs at room temperature. The ethanol-macerated *C. versicolor* raw material was boiled for another 2 hrs. Insoluble substances were separated from supernatant by filtration, to yield a first residue and a first extract. The first residue was added into 10×0.04% NaOH and boiled for another 6 hrs. Insoluble substances were separated from supernatant by filtration, to yield a second residue and a second extract. The extracts were collected, combined, and lyophilized.

Example 2—High Performance Liquid Chromatography Analysis of *Coriolus versicolor* Extract This Example analyzes the chemical fingerprints of the *C. versicolor* extract by high performance liquid chromatography (HPLC). The *C. versicolor* extract was obtained using the extraction schemes illustrated in FIG. 1A, 1B, or by macerating the raw material of *C. versicolor* in ethanol for 18 hrs.

Briefly, one hundred ug/uL of the EtOH extract was subject to high performance liquid chromatography (HPLC) analysis using an Agilent 1200 series HPLC system (Binary Pump SL, G1312B) equipped with a PDA detector (G1315C) and an autosampler (G1367C). The chromatographic column (4.6×250 mm) was packed with ODS-bonded silica gel (Lichrospher 100 RP C18, EC 5 um), and the column temperature was maintained at room temperature during the separation.

Five microliters of the *C. versicolor* extract was injected into the HPLC system. HPLC was performed at a flow rate of 1.0 ml/min using a mixture of water and acetonitrile as the mobile phase. Gradient elution methodology was adopted as illustrated in Table 1. Peak detection was achieved using an Agilent 1200 series of fast scanning photodiode array detector set at 210, 254, and 280 nm. FIGS. 2A-C show the chemical profile of the *C. versicolor* ethanol extract following HPLC.

TABLE 1

HPLC Gradient elution profile applied for fingerprint analysis of the *C. versicolor* extracts obtained using the extraction schemes of FIGS. 1A and 1B

| Time (min) | Water | Acetonitrile | Elution |
|---|---|---|---|
| 0-2 | 95 | 5 | Isocratic |
| 2-25 | 95→10 | 5→90 | Linear gradient |
| 25-27 | 10 | 90 | Isocratic |
| 27-30 | 10→95 | 90→5 | Linear gradient |
| 30-35 | 95 | 5 | Isocratic |

Example 3—Gas Chromatography-Mass Spectrometry Analysis of *Coriolus versicolor* Extract This Example further analyzes the chemical fingerprints of the *C. versicolor* extract by gas chromatography-mass spectrometry (GC-MS). The *C. versicolor* extract was obtained using the extraction scheme illustrated in FIG. 1A or by macerating the raw material of *C. versicolor* in ethanol for 18 hrs.

The *C. versicolor* extract was subjected to silylation before analysis by GC-MS. In brief, 100 ul of the extract (30 ug/μL) in acetonitrile was transferred to a 1 ml reaction vial (Alltech), followed by the addition of 50 ul of pyridine and 50 ul of a derivatizing agent BSTFA [N, O-bis(trimethylsilyl) trifloroacetamide], which reacts with a wide range of polar compounds, thereby replacing labile hydrogen atoms of the polar compounds with a —$Si(CH_3)_3$ group. After incubation at 70° C. for 2 hrs, the mixture was ready for GC-MS analysis.

The mixture was analyzed by GC-MS using (GC: Agilent, 7890A; MS: Agilent, 5975C) and a HP-5MS column (30 m×250 um×0.25 um). Helium with a split ratio of 1:50 was used as the carrier gas, and 1 ul helium at a flow rate of 1 ml/min was injected into the column. The initial oven temperature was 70° C., which was maintained for 1 min, increased to 180° C. at a rate of 10° C. per min, maintained at 180° C. for 2 min, increased to 280° C. at a rate of 10° C. per min, and maintained at 280° C. for 3 min. The injector temperature was 275° C.; the interface temperature was 250° C., the ion source temperature was 230° C., and the electron impact ionization (EI) was performed at 200 eV. Mass spectra were analyzed in the range of 50-700 atom mass units (amu) for a run time of 22 min, and the data was processed using Agilent G1701EA chemstation. FIG. 3 shows the chromatographic profile of the *C. versicolor* ethanol extracts following GC-MS analysis.

Example 4—Fractionation of *C. versicolor* Extract

The *C. versicolor* ethanol extract (MPUB-EtOH) obtained using the extraction scheme illustrated in FIG. 1A was further separated into 5 fractions (FIG. 4), using a Waters preparative liquid chromatography system that was equipped with a 1525 binary HPLC pump, a 2998 photodiode array detector and a Waters fraction collector III. The fractionation was performed using a reversed-phase column (Lichrospher 100 RP C18, EC 5 um), and the detection wavelength was set at 210, 254 and 280 nm. The gradient program consisted of two solvents (A) water and (B) acetonitrile at a flow of 1 ml/min as follows: 0-16 min, 10-90% B; 16-18 min, 90% B and 18-22 min, 10% B.

Example 5—Effects of *Coriolus versicolor* Extract on Cytokine Production

Figure 5A:
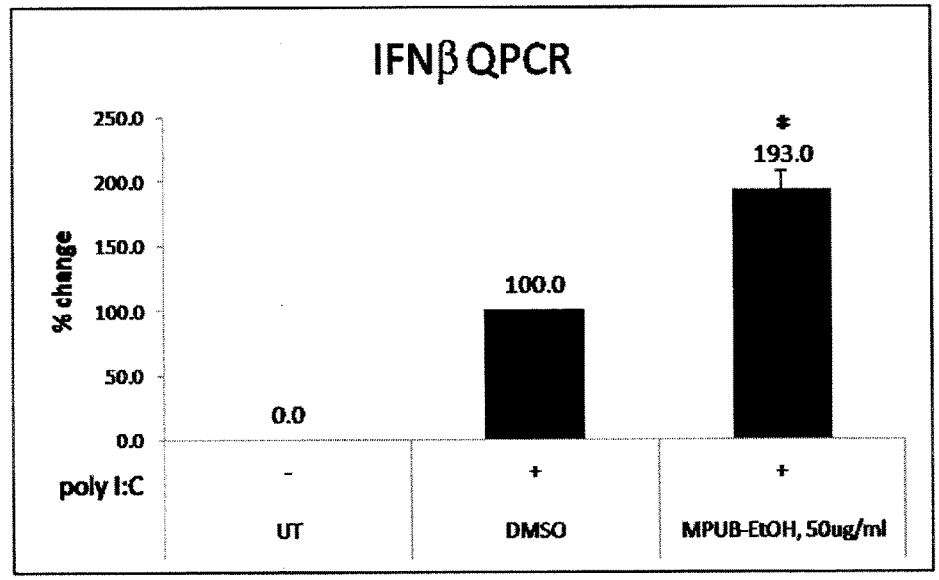
FIGS. 5A-B show that *C. versicolor* extract (MPUB-EtOH) increased INFβ production (A) and reduced IL10 production (B) in primary human blood macrophages treated with polyinosine-polycytidylic acid (poly(I:C)). All data were plotted as mean values±SD of at least 3 independent experiments. A p value of <0.05 (*) or <0.001 (**) was considered statistically significant.
Figure 5B:
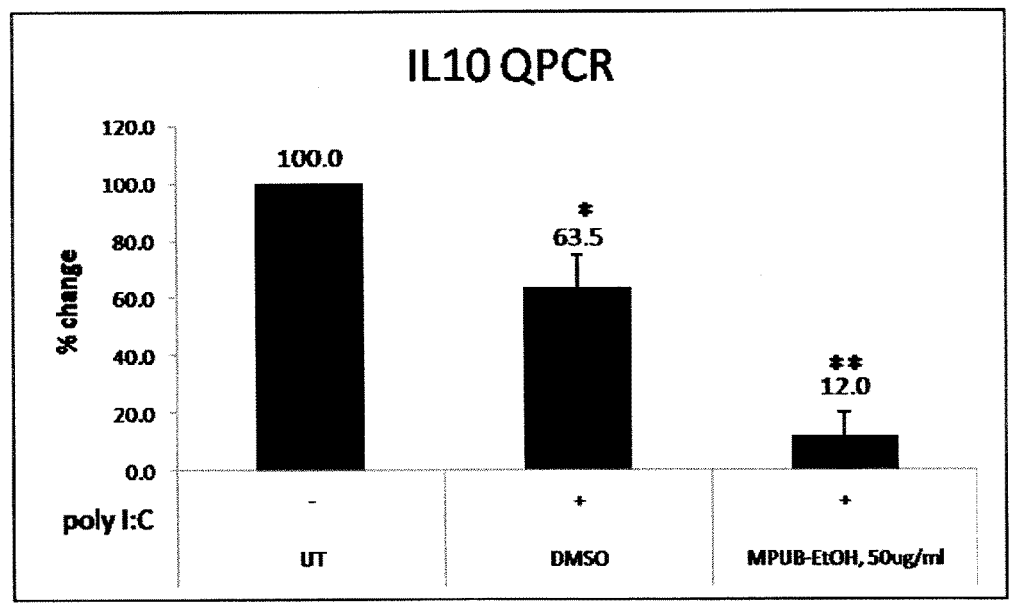

To investigate the effect of *C. versicolor* extract (MPUB-EtOH) on IFNβ and IL-10 production, primary human blood macrophages were pretreated with MPUB-EtOH at 50 ug/ml for 18 hrs. The cells were then treated with polyinosine-polycytidylic acid (poly I:C) (50 ug/ml) for 3 hrs. IFNβ mRNA and IL-10 mRNA levels were analyzed by TaqMan Gene Expression Assays. As shown in FIGS. 5A-B, the *C. versicolor* extract increased IFNβ production and inhibited IL-10 production.

Figure 6A:
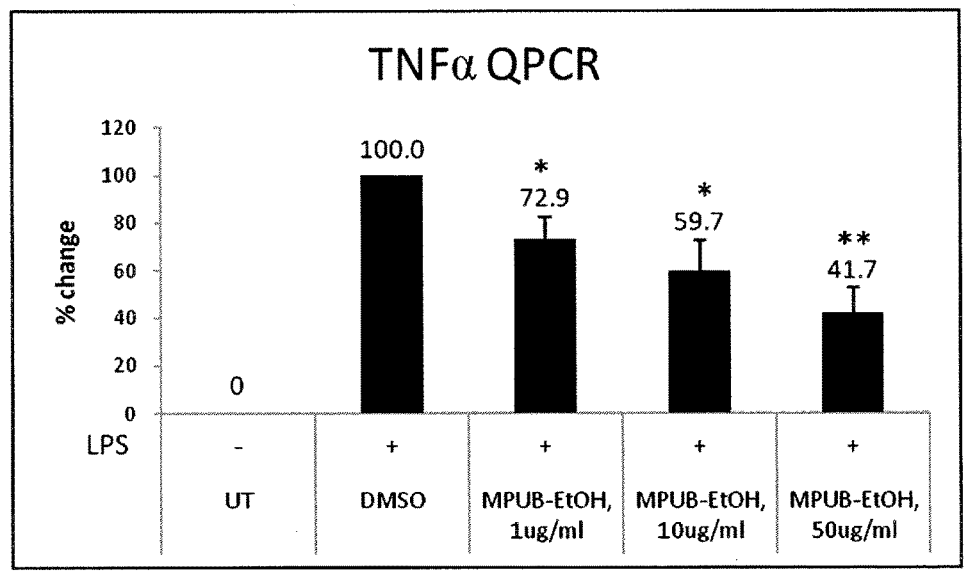
FIGS. 6A-B show that *C. versicolor* extract (MPUB-EtOH) reduced LPS-induced TNFα production. All data were plotted as mean values±SD of at least 3 independent experiments. A p value of <0.05 (*) or <0.001 (**) was considered statistically significant.
Figure 6B:
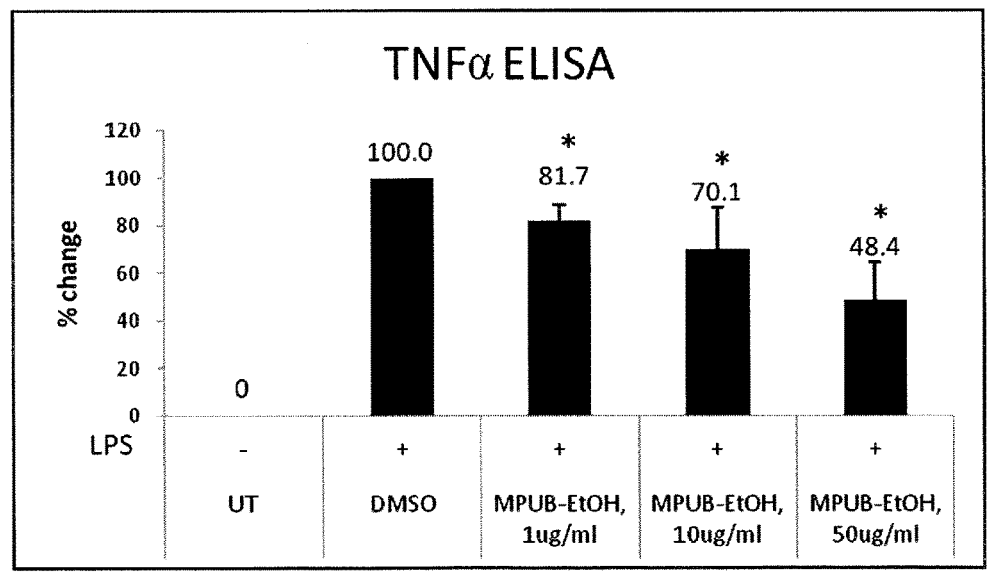

To investigate the effect of *C. versicolor* extract (MPUB-EtOH) on LPS-induced TNFα production, primary human blood macrophages were pretreated with MPUB-EtOH at various concentrations (1, 10 and 50 ug/ml) for 18 hrs. The cells were then treated with lipopolysaccharides (LPS) (1 ng/ml) for 3 and 24 hrs. TNFα mRNA levels and protein levels were analyzed by TaqMan Gene Expression Assays and enzyme-linked immunosorbent assays (ELISA), respectively. As shown in FIGS. 6A-B, *C. versicolor* extract reduced TNFα production in a dose-dependent manner.

Figure 7:
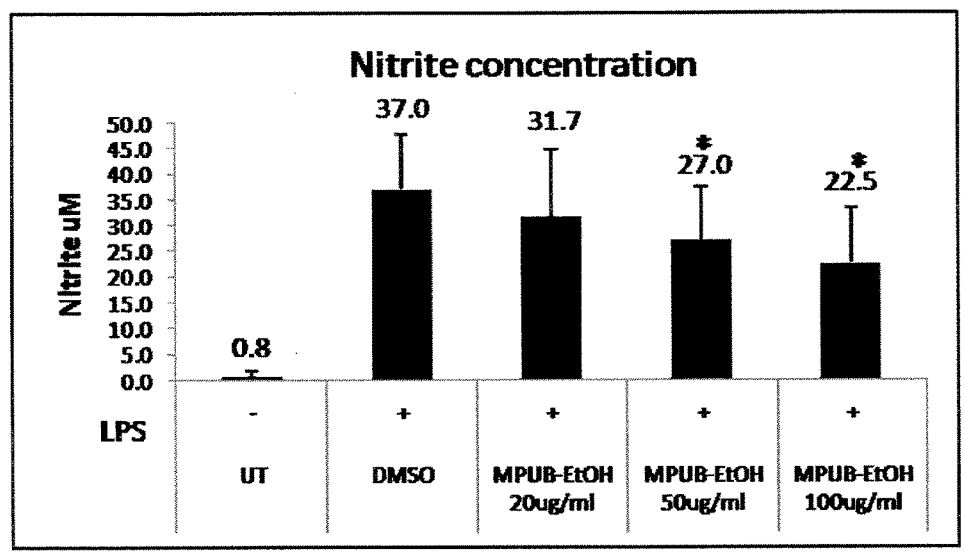
FIG. 7 shows that *C. versicolor* extract (MPUB-EtOH) reduced LPS-induced nitrite production. All data were plotted as mean values±SD of at least 3 independent experiments. A p value of <0.05 (*) was considered statistically significant.

To investigate the effect of *C. versicolor* extract (MPUB-EtOH) on LPS-induced nitrite production, mouse macrophages (RAW 264.7) were pretreated with MPUB-EtOH at various concentrations (20, 50 and 100 ug/ml) for 24 hrs. The cells were then treated with LPS (100 ng/ml) for 18 hrs, and nitrite concentrations (uM) were measured by Griess Reagent. As shown in FIG. 7, *C. versicolor* extract inhibited nitrite production in a dose-dependent manner.

Example 6—Determination of Antiviral Effects of *Coriolus versicolor* Extract To investigate the antiviral effects of *C. versicolor* extract, human neuronal cells (SKNSH) were pretreated with the MPUB-EtOH at 10 ug/ml for 18 hrs. Culture supernatants were reserved for sequential incubation. The cells were then infected with herpes simplex virus (HSV) at a m.o.i. (multiplicity of infection) of 0.01 for 1 hr. After viral infection, the cells were washed twice with PBS and incubated with the reserved culture supernatants for another 18 hrs. The culture supernatants were collected for determining viral titers, measured by the titration of tissue culture infectious dose$_{50}$ (TCID$_{50}$) during infection of T98G (human glioblastoma line) cells.

Figure 8A:
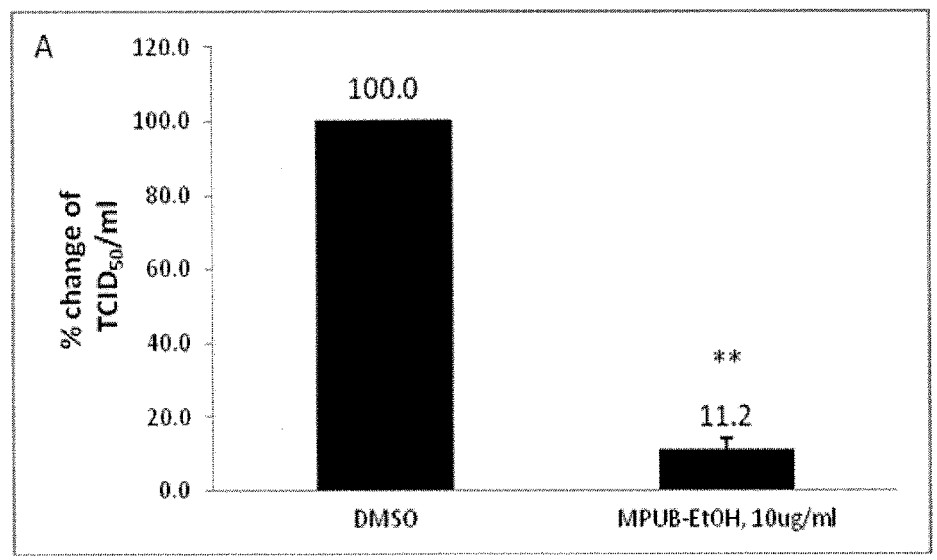
FIGS. 8A-C show the antiviral effects of *C. versicolor* extract (MPUB-EtOH). (A) shows the reduction of herpes simplex virus (HSV) viral titers by *C. versicolor* extract. The *C. versicolor* extract (MPUB-EtOH) was fractionated into fractions 1-5 as shown in FIG. 4. Fractions 4-5 were cytotoxic (data not shown), and thus, were not further examined for antiviral effects. (B) shows the reduction of HSV viral titers by fractions 1-3 of the *C. versicolor* extract (MPUB-EtOH). (C) shows the reduction of HSV viral titers by fraction 3 of the *C. versicolor* extract (MPUB-EtOH). A p value of <0.001 (**) was considered statistically significant.

MPUB-EtOH was further factionated into five fractions as described in Example 4. SKNSH cells were pretreated with MPUB-EtOH-1, -2 and -3, and infected with HSV virus as described above. The viral titers (TCID$_{50}$) of culture supernatants were measured. MPUB-EtOH-4 and -5 were cytotoxic to the cells (data not shown) and, thus, were not investigated further for antiviral effects. All data shown in FIGS. 8A and 8C were plotted as mean values±SD of at least 3 independent experiments. A p value of <0.001 (**) was considered statistically significant.

Figure 8B:
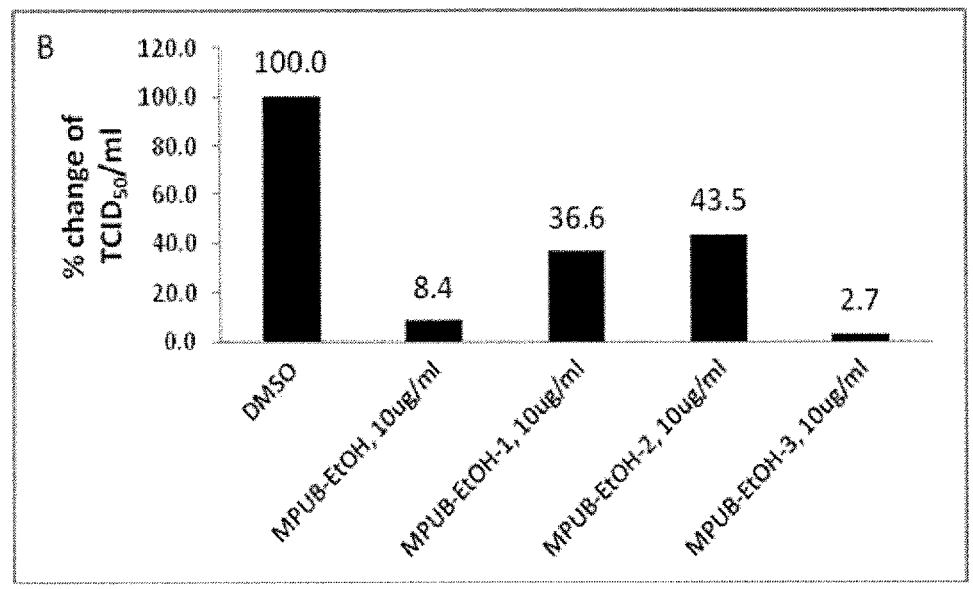
Figure 8C:
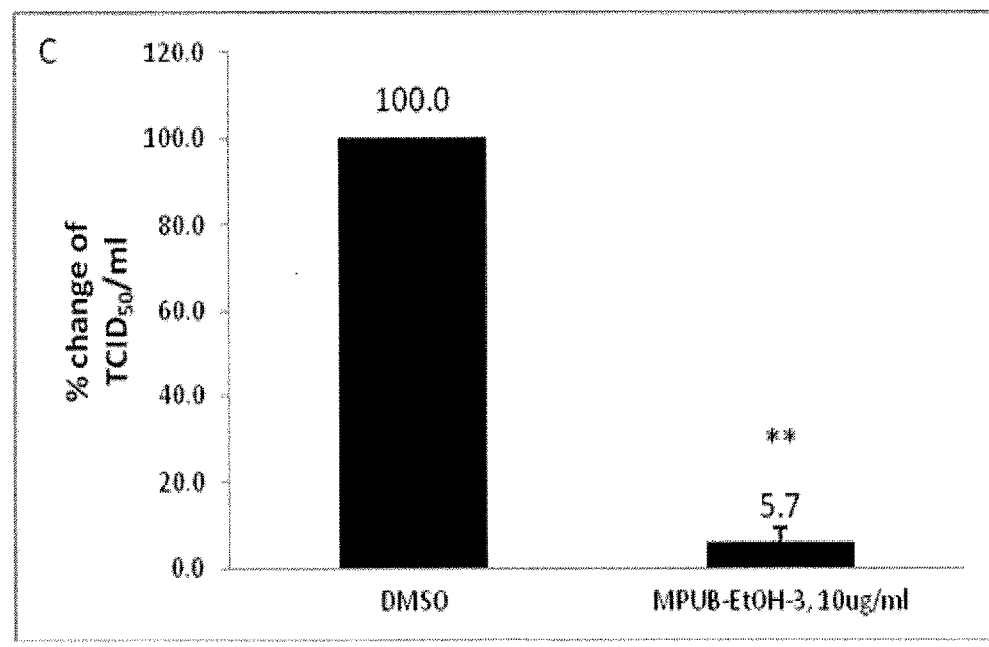

As shown in FIG. 8, the *C. versicolor* extract significantly reduced viral titers in culture supernatants, wherein fraction 3 exhibited the most potent antiviral effects (FIGS. 8B and 8C).

Example 7—Effects of *Coriolus versicolor* Extract on MMP-3 Expression

Figure 9:
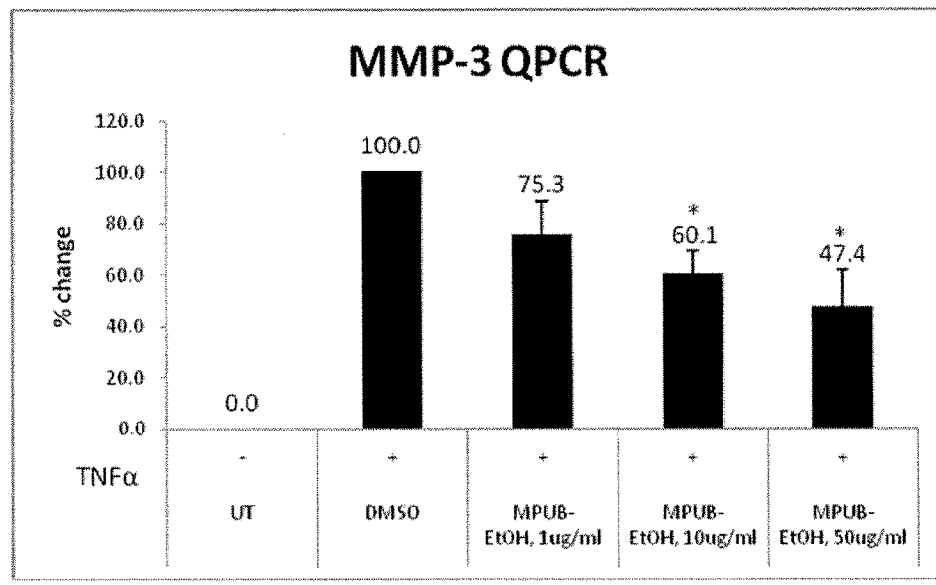
FIG. 9 shows that *C. versicolor* extract (MPUB-EtOH) reduced MMP-3 expression. A p value of <0.05 (*) was considered statistically significant.

This Example shows that *C. versicolor* extract reduces MMP-3 expression (FIG. 9). Briefly, glioblastoma (T98G; brain cells) cells were pretreated with MPUB-EtOH at different concentrations (1, 10 and 50 ug/ml) for 18 hrs, and then treated with recombinant human TNFα (10 ng/ml) for 3 hrs. MMP-3 mRNA levels were analyzed by TaqMan Gene Expression Assays. All data were plotted as mean values±SD of at least 3 independent experiments. A p value of <0.05 (*) was considered statistically significant.

Example 8—Determination of Antiviral Effects of *Coriolus versicolor* Extract In Vivo To investigate the antiviral effects of *C. versicolor* extract in vivo, 3-week-old male BALB/c mice (15 mice per group) were administrated intraperitoneally (ip) with dimethyl sulfoxide (DMSO) (solvent for MPUB-EtOH) or MPUB-EtOH (250 mg/kg) once a day at 24 hr intervals for 7 days.

Figure 10:
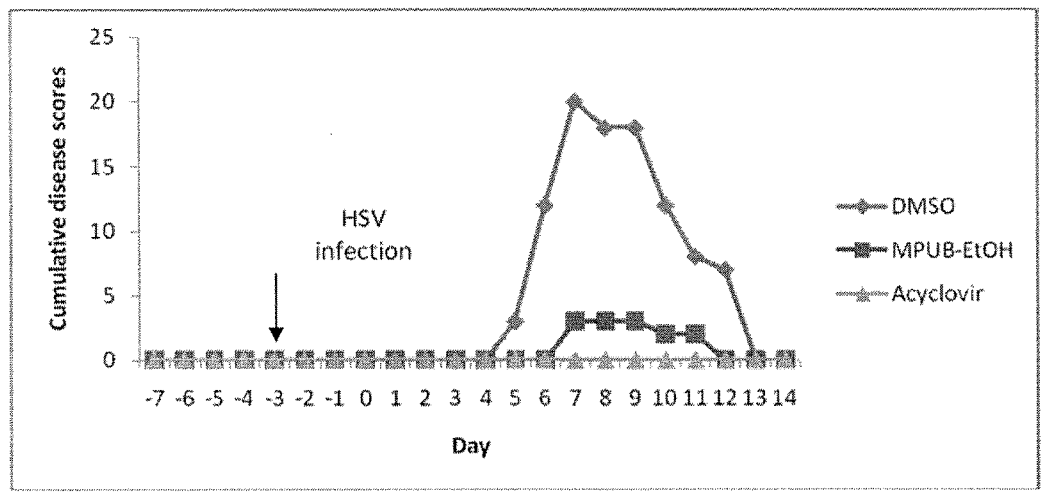
FIG. 10 shows that *C. versicolor* extract (MPUB-EtOH) reduced the severity of HSV infection in mice.

Briefly, the mice were infected with inoculation of HSV ip at 1×10$^5$ TCID$_{50}$/ml at day 0. DMSO, MPUB-EtOH or acyclovir (10 mg/kg) were administrated ip once a day at 24 hr intervals for 5 days starting 1 hr after infection. The mice were inspected daily and the disease severity was measured by hind-limb(s) paralysis based on the following scoring system: 0, no paralysis; 1, obvious difficulty in movement of hind limbs; 2, one hind limb incomplete paralysis; 3, one hind limb complete paralysis; 4, both hind limbs incomplete paralysis; 5, both hind limbs complete paralysis. As shown in FIG. 10, *C. versicolor* extract (MPUB-EtOH) significantly reduced the severity of HSV infection in mice, as compared to the DMSO-treated controls. The antiviral effects of *C. versicolor* extract were comparable to that of acyclovir.

Example 9—Effects of *Coriolus versicolor* Extracts and 9-KODE Methyl Ester on MMP-3 Expression This Example shows that ethanol extract of *C. versicolor* as well as 9-oxo-10E,12E-octadecadienoic acid methyl ester (9-KODE methyl ester) inhibit TNF-α induced matrix metalloproteinase 3 (MMP3) expression, and can be used to inhibit or reduce tumor metastasis.

Figure 11:
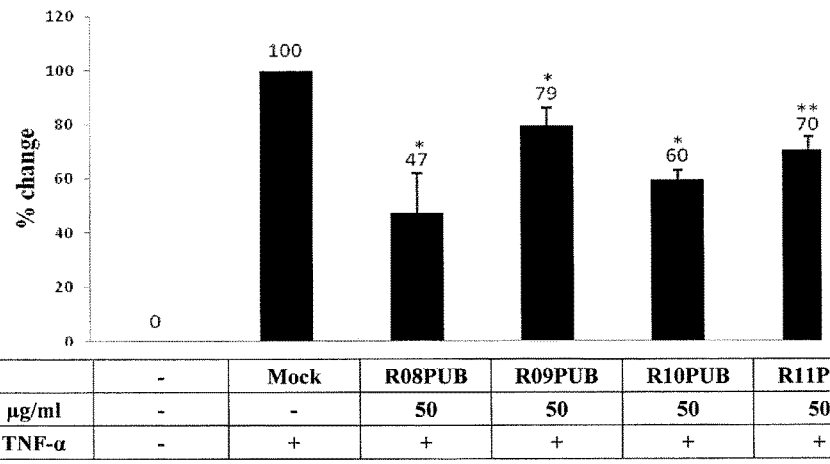
FIG. 11 shows that different batches of ethanol extract of *C. versicolor* (R08PUB, R09PUB, R10PUB and R11PUB) at 50 µg/ml suppressed TNF-α induced MMP-3 mRNA level. Briefly, glioblastoma (T98G, brain cells) cells were pretreated with different batches of ethanol extract of *C. versicolor* for 18 hr, and then treated with recombinant human TNF-α (10 ng/ml) for 3 hr. MMP-3 mRNA levels were analyzed by TaqMan Gene Expression Assays. All data were plotted as mean values±SD of at least 3 independent experiments. * P<0.05, ** P<0.01 was considered statistically significant. ("R08," "R09," and "R11" indicate the year of harvest of *C. versicolor* is 2008, 2009, and 2011, respectively).
Figure 12:
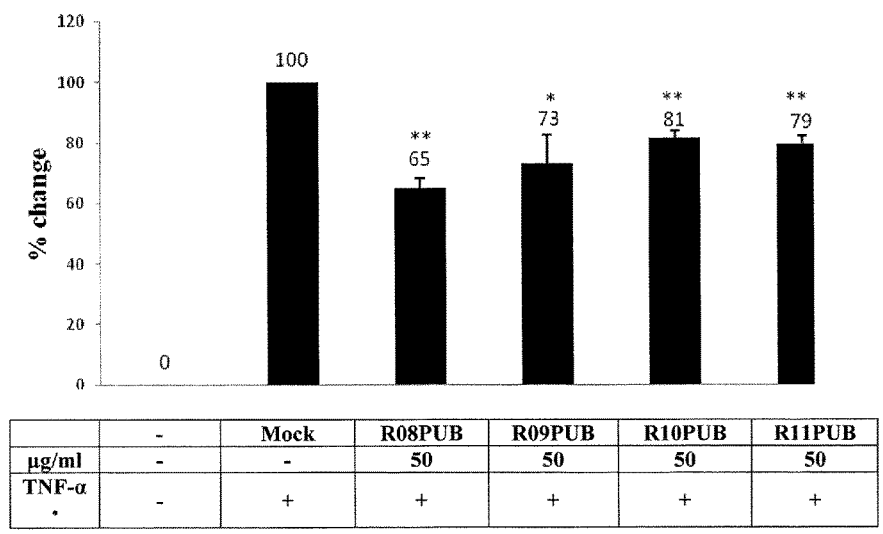
FIG. 12 shows that different batches of ethanol extract of *C. versicolor* (R08PUB, R09PUB, R10PUB and R11PUB) at 50 µg/ml inhibited TNF-α induced MMP-3 protein expression. Briefly, glioblastoma (T98G, brain cells) cells were pretreated with different batches of ethanol extract of *C. versicolor* for 18 hr, and then treated with recombinant human TNF-α (10 ng/ml) for another 24 hr. MMP-3 protein expressions were analyzed by enzyme-linked immunosorbent assays (ELISA). All data were plotted as mean values±SD of at least 3 independent experiments. * P<0.05, ** P<0.01 was considered statistically significant.
Figure 20:
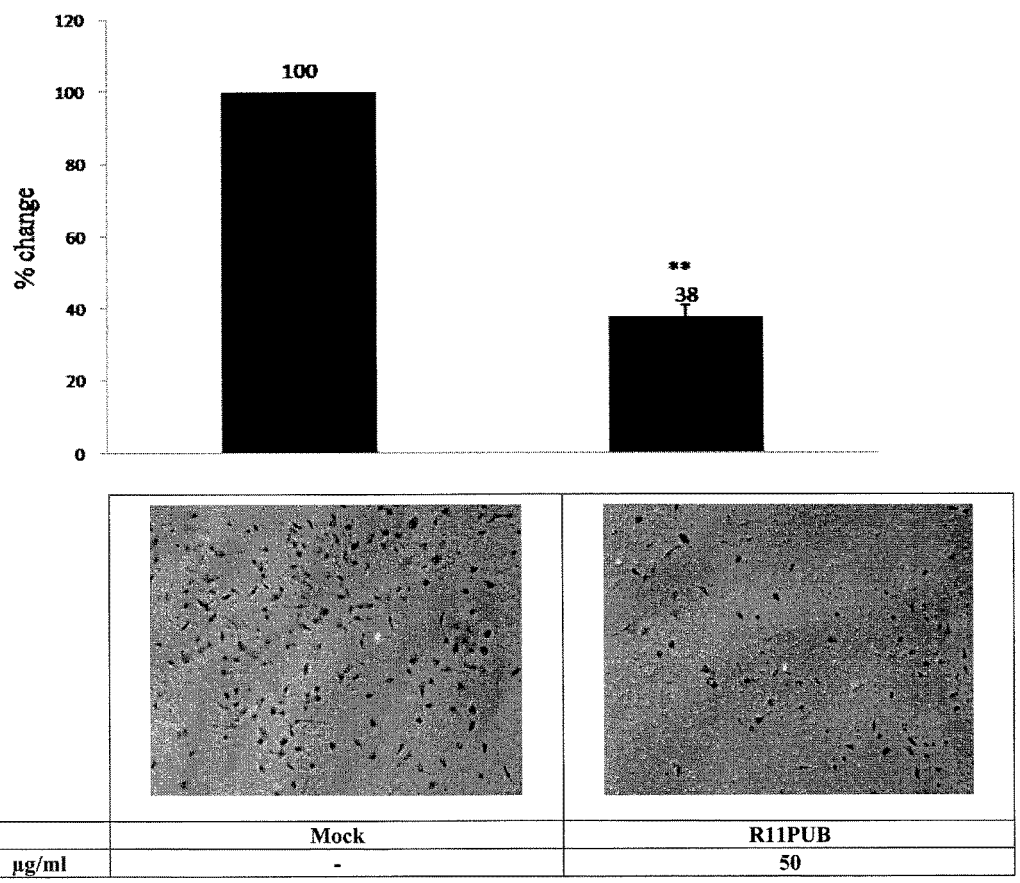
FIG. 20 shows that ethanol extract of C. versicolor (R11PUB) at 50 μg/ml reduced T98G cell invasiveness. Cell invasiveness was studied using Matrigel Invasion Chamber. Glioblastoma (T98G, brain cells) cells were treated with R11PUB for 18 hr, and the cells were allowed to invade through the matrices for another 24 hr. The number of invading cells was quantified by counting under a light microscope. All data were plotted as mean values±SD of at least 3 independent experiments. ** P<0.01 was considered statistically significant.

As shown in FIGS. 11 and 12, *Coriolus versicolor* (PUB) extracts regulate TNF-α induced MMP3 expression as well as the migration of human glioma T98G cells. Different batches of ethanol extract of *C. versicolor* (R08PUB, R09PUB, R10PUB and R11PUB) at 50 μg/ml suppressed both TNF-α induced MMP-3 mRNA and protein expressions (FIGS. 11 and 12). Specifically, R11PUB ethanol extract at 50 μg/ml reduced T98G cell invasiveness (FIG. 20).

Figure 13:
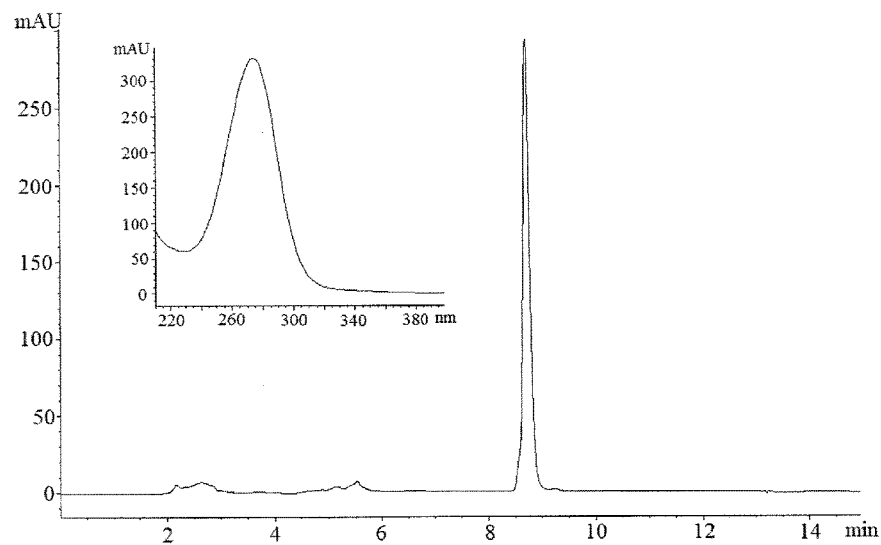
FIG. 13 shows HPLC chromatogram and UV absorbance of a compound isolated from *C. versicolor* (also referred to herein as "Cove-1"). The compound Cove-1 was purified by reversed-phase HPLC using gradient elution from 20% to 90% of acetonitrile at a flow rate of 1 ml/min. A single peak eluted at approximate 8.5 min was detected using Photodiode Array detector at 280 nm. The UV absorbance of compound Cove-1 maximized at 277 nm, which revealed that the compound Cove-1 has a conjugated carbonyl group.
Figure 14A:
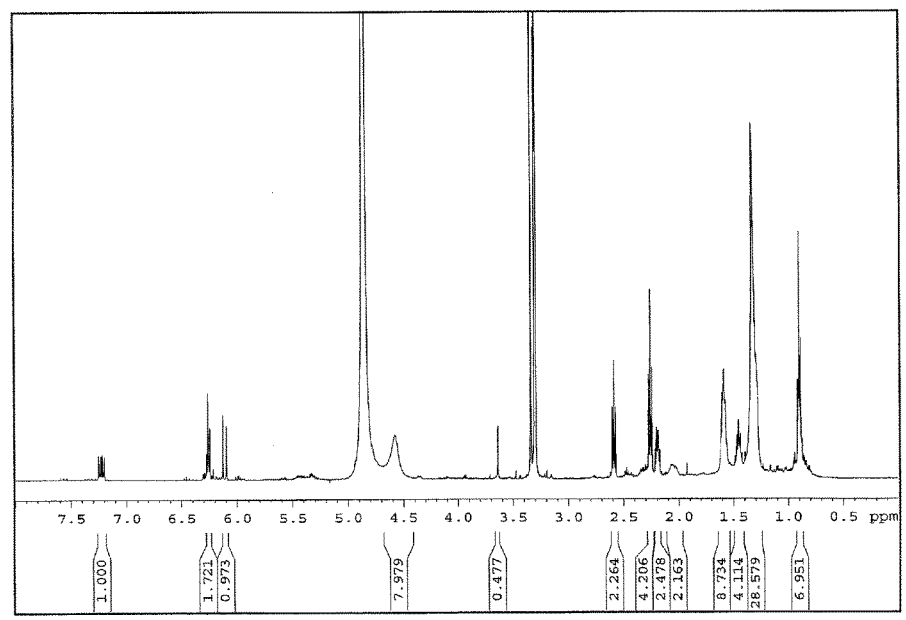
FIGS. 14A-B show the $^1$H (A) and $^{13}$C NMR (B) spectra of compound Cove-1. The structure of compound Cove-1 was elucidated by a Bruker 500 MHz DRX NMR spectrometer, operating at 500 MHz for 1H and at 125.765 MHz for $^{13}$C NMR, using methanol-d as the solvent. The $^1$H NMR spectra of compound Cove-1 showed signals at 0.9, 1.3-1.4, 1.45, 1.58, 2.19, 2.25, 2.58, 3.33, 6.12, 6.26 and 7.22. The $^{13}$C NMR spectra of compound Cove-1 showed signals at 14.5, 23.7, 25.7, 26.3, 29.7, 30.3, 30.3, 30.3, 32.7, 34.3, 35.4, 41.1, 50.0, 128.9, 130.4, 145.5, 147.6, 178.2 and 204.1.
Figure 14B:
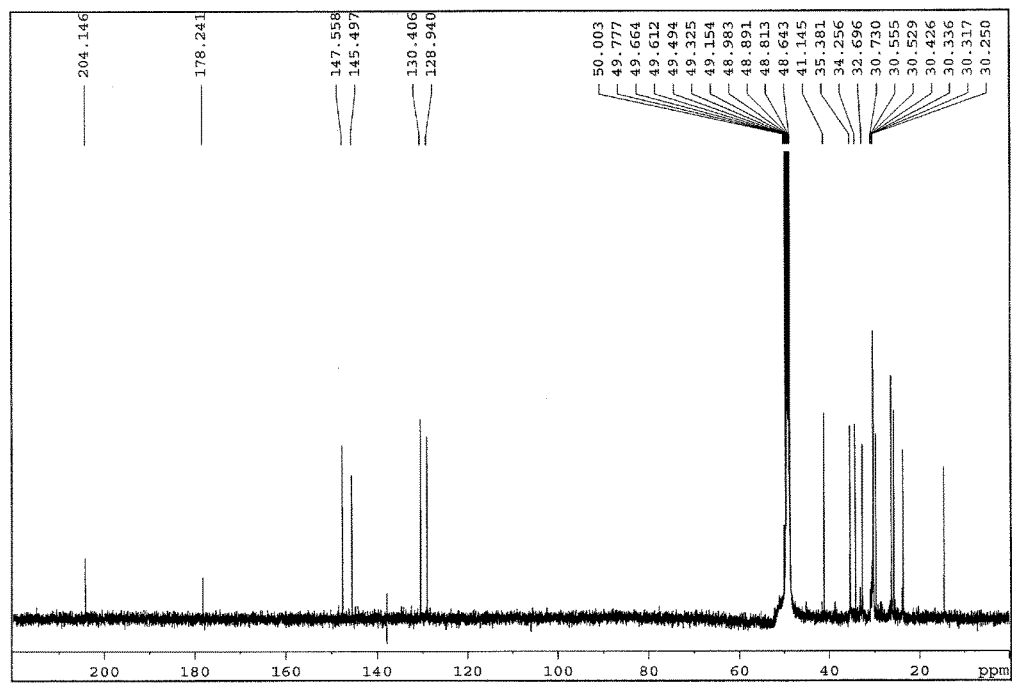
Figure 15:
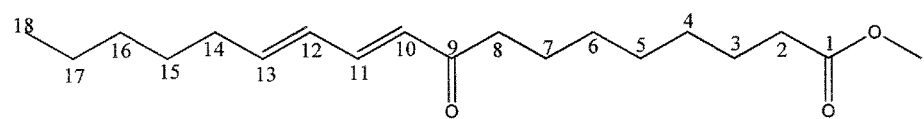
FIG. 15 shows the chemical structure of compound Cove-1. $^1$HNMR (500 MHz): δ0.9 (3H, H-18), 1.3-1.4 (10H, H-4, 5, 6, 16, 17), 1.45 (2H, H-15), 1.58 (4H, H-3, 7), 2.19 (2H, H-14), 2.25 (2H, H-2), 2.58 (2H, H-8), 3.33 (3H, CH$_3$OOC), 6.12 (1H, H-10), 6.26 (2H, H-12, 13), 7.22 (1H, H-11). $^{13}$C NMR (125 MHz): δ14.5 (C-18), 23.7 (C-17), 25.7 (C-7), 26.3 (C-3), 29.7 (C-15), 30.3 (C-4*), 30.3 (C-5*), 30.3 (C-6*), 32.7 (C-16), 34.3 (C-14), 35.4 (C-2), 41.1 (C-8), 50.0 (OCH$_3$), 128.9 (C-10), 130.4 (C-12), 145.5 (C-11), 147.6 (C-13), 178.2 (C-1) and 204.1 (C-9). * Interchangeable. The result was confirmed by Dept 135, HSQC and $^1$H-$^1$H COSY. Compound Cove-1 showed ion peaks at m/z 55, 67, 81, 95, 151, 166, 276, 308. In comparison of the spectroscopic data with the data reported in the literature, compound Cove-1 was identified as 9-oxo-10E,12E-octadecadienoic acid methyl ester (9-KODE methyl ester).
Figure 16:
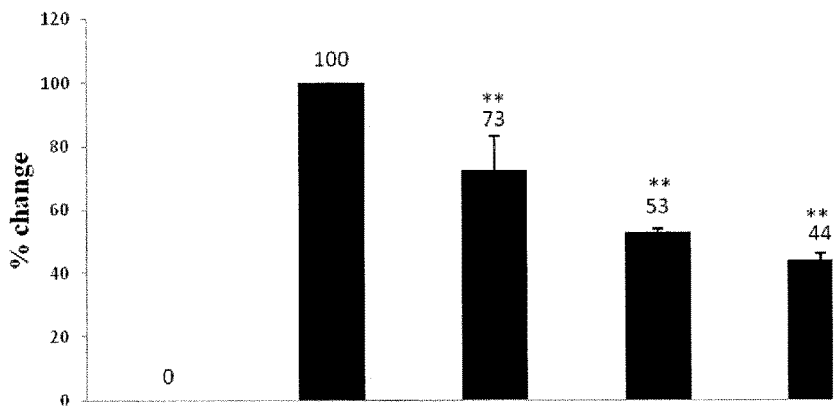
FIG. 16 shows that purified compound Cove-1 at 10, 25 and 50 μg/ml suppressed TNF-α induced MMP-3 mRNA level. Briefly, glioblastoma (T98G, brain cells) cells were pretreated with purified Cove-1 compound for 18 hr, and then treated with recombinant human TNF-α (10 ng/ml) for 3 hr. MMP-3 mRNA levels were analyzed by TaqMan Gene Expression Assays. All data were plotted as mean values±SD of at least 3 independent experiments. ** P<0.01 was considered statistically significant.
Figure 17:
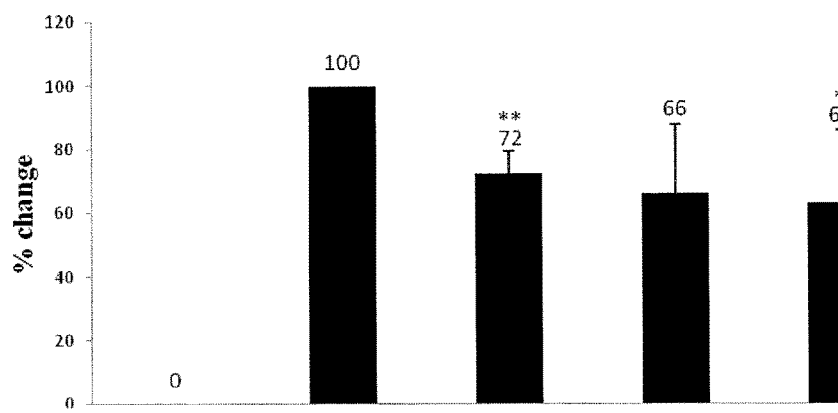
FIG. 17 shows that purified compound Cove-1 at 10, 25 and 50 μg/ml inhibited TNF-α induced MMP-3 protein expression. Briefly, glioblastoma (T98G, brain cells) cells were pretreated with purified compound Cove-1 for 18 hr, and then treated with recombinant human TNF-α (10 ng/ml) for another 24 hr. MMP-3 protein expressions were analyzed by enzyme-linked immunosorbent assays (ELISA). All data were plotted as mean values±SD of at least 3 independent experiments. * P<0.05, ** P<0.01 was considered statistically significant.

9-oxo-10E,12E-octadecadienoic acid methyl ester (9-KODE methyl ester; also referred to herein as "Cove-1") is isolated from *C. versicolor* (FIGS. 13-15). As shown in FIGS. 16 and 17, 9-KODE methyl ester regulates TNF-α induced matrix metalloproteinase 3 expression and migration of human glioma T98G cells. Specifically, 9-KODE methyl ester at 10, 25 and 50 μg/ml suppressed both TNF-α, induced MMP-3 mRNA and protein expressions (FIGS. 16 and 17).

Figure 18:
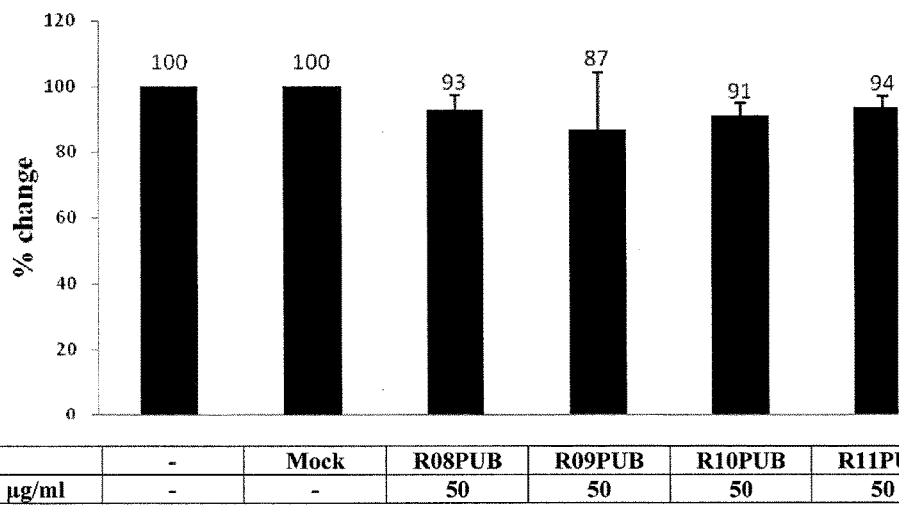
FIG. 18 shows that there were no significant differences in the metabolic activities of the cells incubated with different batches of ethanol extract of C. versicolor (R08PUB, R09PUB, R10PUB and R11PUB) at 50 μg/ml on T98G cells. MTT (3-[4,5-dimethylthiazol-2-yl]-2,5-di-phenyltetrazolim bromide) assays were performed over a time course of 48 hr. All data were plotted as mean values±SD of at least 3 independent experiments.
Figure 19:
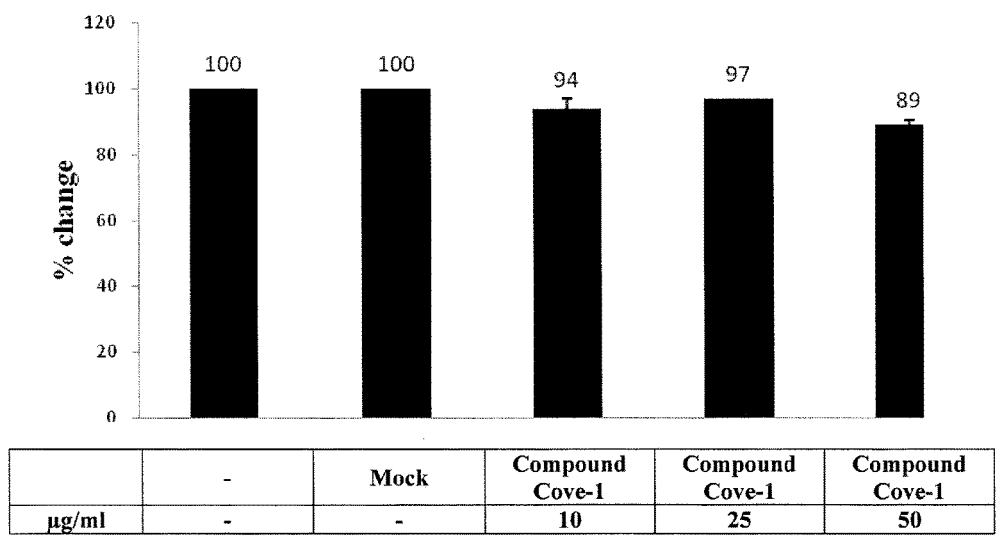
FIG. 19 shows that there were no significant differences in the metabolic activities of the cells incubated with the purified compound (Cove-1) at 10, 25 and 50 μg/ml on T98G cells. MTT (3-[4,5-dimethylthiazol-2-yl]-2,5-di-phenyltetrazolim bromide) assays were performed over a time course of 48 hr. All data were plotted as mean values±SD of at least 3 independent experiments. The results show that compound Cove-1 does not have significant toxicity.

In addition, the results show that different batches of ethanol extract of *C. versicolor* or 9-KODE methyl ester has almost no cytotoxic effects (FIGS. 18 and 19).

Figure 21:
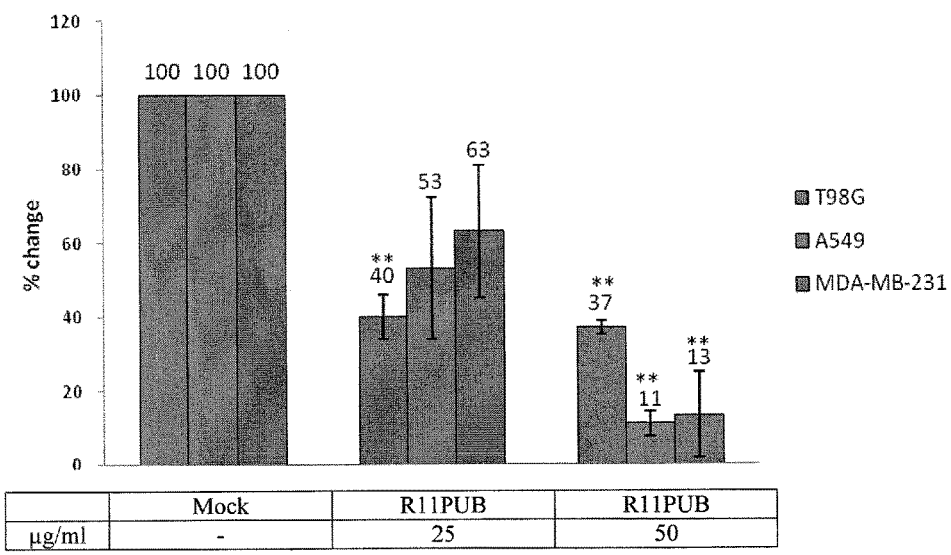
FIG. 21 shows that the ethanol extract of C. versicolor (R11PUB) at 25 and 50 μg/ml reduced cell invasiveness. Cell invasiveness was studied using a Matrigel Invasion Chamber. Glioblastoma (T98G), lung carcinoma (A549), and breast adenocarcinoma (MDA-MB-231) cells were treated with R11PUB for 18 hr, and then the cells were allowed to invade through the matrices for another 24 hr. The number of invading cells was quantified by counting under a light microscope. All data were plotted as mean values±SD of at least 3 independent experiments. ** P<0.01 was considered statistically significant.

Example 10—Effects of *Coriolus versicolor* Extracts and 9-KODE Methyl Ester on Reduction of Invasiveness of Cancer Cells This Example shows that the ethanol extract of *C. versicolor* (R11PUB) dose-dependently reduced the invasiveness of cancer cells, including T98G cells, A549 cells, and MDA-MB-231 cells (FIG. 21).

Specifically, the effect of C. versicolor on cancer cell invasiveness was studied using a Matrigel Invasion Chamber. Glioblastoma (T98G), lung carcinoma (A549), and breast adenocarcinoma (MDA-MB-231) cells were treated with one batch of ethanol extract of C. versicolor (R11PUB) for 18 hr, and then the cells were allowed to invade through the matrices for another 24 hr. The number of invading cells was quantified by counting under a light microscope. All data were plotted as mean values±SD of at least 3 independent experiments. ** P<0.01 was considered statistically significant. As shown in FIG. 21, ethanol extract of C. versicolor (R11PUB) at 25 and 50 µg/ml reduced cell invasiveness.

Figure 22:
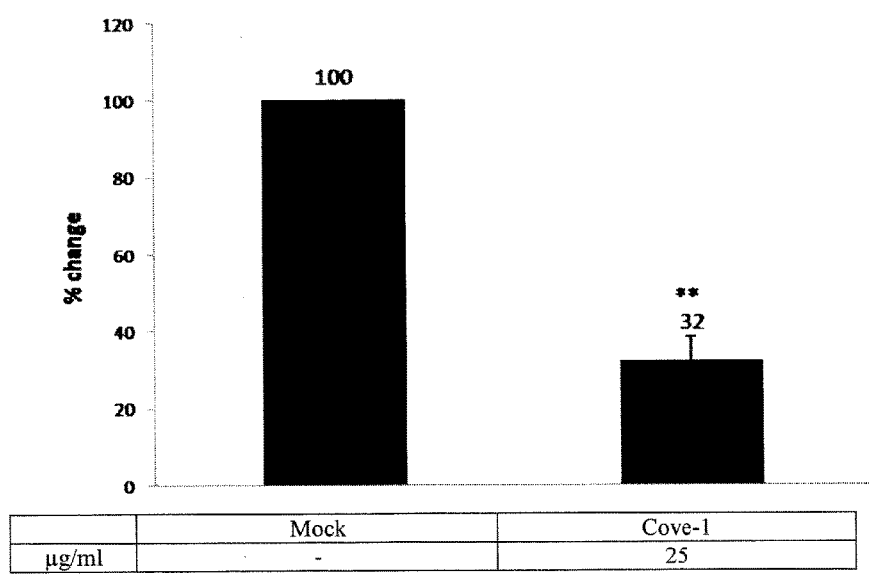
FIG. 22 shows that 9-KODE methyl ester (Cove-1) at 25 μg/ml reduced T98G cell invasiveness. Cell invasiveness was studied using a Matrigel Invasion Chamber. Glioblastoma (T98G) cells were treated with Cove-1 for 18 hr, and then the cells were allowed to invade through the matrices for another 24 hr. The number of invading cells was quantified by counting under a light microscope. All data were plotted as mean values±SD of at least 3 independent experiments. ** P<0.01 was considered statistically significant.

In addition, 9-oxo-10E,12E-octadecadienoic acid methyl ester (9-KODE methyl ester; also referred to herein as "Cove-1") (25 µg/ml) reduced the invasiveness of T98G significantly (FIG. 22).

Specifically, the effect of 9-KODE methyl ester on cell invasiveness was studied using Matrigel Invasion Chamber. Glioblastoma (T98G) cells were treated with 9-KODE methyl ester for 18 hr, and then the cells were allowed to invade through the matrices for another 24 hr. The number of invading cells was quantified by counting under a light microscope. All data were plotted as mean values±SD of at least 3 independent experiments. ** P<0.01 was considered statistically significant. As shown in FIG. 22, 9-KODE methyl ester at 25 µg/ml reduced T98G cell invasiveness.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

REFERENCES

Yang C L, Chik S C, Li J C, Cheung B K, Lau A S (2009) Identification of the bioactive constituent and its mechanisms of action in mediating the anti-inflammatory effects of black cohosh and related *Cimicifuga* species on human primary blood macrophages. *J Med. Chem.* 52:6707-15.

Cheng S M, Li J C, Lin S S, Lee D C, Liu L, Chen Z, Lau A S (2009) HIV-1 transactivator protein induction of suppressor of cytokine signaling-2 contributes to dysregulation of IFN{gamma} signaling. *Blood.* 113:5192-201.

Law A H Y, Lee D C W, Cheung B K W, Yim H C H, Lau A S (2007) A Role for the nonstructural protein of SARS-CoV in Chemokine Dysregulation. *J. Virology.* 81:416-22.

Lee D C, Yang C L, Chik S C, Li J C, Rong J H, Chan G C, Lau A S (2009) Bioactivity-guided identification and cell signaling technology to delineate the immunomodulatory effects of *Panax ginseng* on human promonocytic U937 cells. *J Transl Med.* 7:34.

Kuklev et al. (1997) Synthesis of Keto- and Hydroxydienoic Compounds from Linoleic Acid, *Chemistry and Physics of Lipids,* 85: 125-134.

Andreou et al. (2009), Biosynthesis of Oxylipins in Non-mammals, *Progress in Lipid Research,* 48:148-170.

We claim:

1. A method for treating cancer or a tumor, comprising administering, to a subject in need of such treatment, an effective amount of a composition comprising 9-oxo-10E,12E-octadecadienoic acid methyl ester, or a salt thereof, wherein the cancer or tumor is selected from the group consisting of glioblastoma, breast carcinoma, and lung carcinoma.

2. The method of claim 1, wherein the subject is a human.

3. A method for treating cancer or a tumor, comprising administering, to a subject in need of such treatment, an effective amount of a composition comprising 9-oxo-10E,12E-octadecadienoic acid methyl ester, or a salt thereof, wherein the cancer is metastatic cancer and the administration of the composition is used to reduce cancer metastasis.

4. The method of claim 3, wherein the subject is a human.

5. The method according to claim 1, wherein the compound inhibits the expression of MMP3.

6. The method according to claim 1, wherein the compound reduces TNF-α, wherein the compound reduces TNF-α production in tumor cells.

* * * * *